United States Patent
Rapraeger et al.

(10) Patent No.: US 10,485,849 B2
(45) Date of Patent: *Nov. 26, 2019

(54) SYNDECAN PEPTIDES AND POLYPEPTIDES AS INHIBITORS OF VASCULAR ENDOTHELIAL GROWTH FACTOR RECEPTOR-2 (VEGFR2) AND VERY LATE ANTIGEN-4 (VLA-4)

(71) Applicant: Wisconsin Alumni Research Foundation, Madison, WI (US)

(72) Inventors: Alan Rapraeger, Stoughton, WI (US); Oisun Jung, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/882,065

(22) Filed: Jan. 29, 2018

(65) Prior Publication Data
US 2018/0169185 A1   Jun. 21, 2018

Related U.S. Application Data

(62) Division of application No. 15/043,951, filed on Feb. 15, 2016, now Pat. No. 9,878,007.

(60) Provisional application No. 62/119,466, filed on Feb. 23, 2015.

(51) Int. Cl.
*A61K 45/06* (2006.01)
*A61K 38/17* (2006.01)
*A61K 38/10* (2006.01)
*A61K 38/16* (2006.01)

(52) U.S. Cl.
CPC ............ *A61K 38/177* (2013.01); *A61K 45/06* (2013.01)

(58) Field of Classification Search
CPC ...... A61K 38/177; A61K 45/06; A61K 38/17; A61K 38/10; A61K 38/16
USPC .......... 514/17.9, 18.7, 16.6, 21.5, 21.4, 21.3
See application file for complete search history.

(56) References Cited

U.S. PATENT DOCUMENTS

2007/0054332 A1* 3/2007 Rapraeger .............. A61K 38/08
435/7.23

OTHER PUBLICATIONS

P18827 from UniProt, pp. 1-16. Integrated into UniProtKB/Swiss-Prot Nov. 1, 1990.*
Q90X98 from UniProt, pp. 1-4. Integrated into UniProtKB/TrEMBL Dec. 1, 2001.*

* cited by examiner

*Primary Examiner* — Julie Ha
(74) *Attorney, Agent, or Firm* — Boyle Fredrickson S.C.

(57) ABSTRACT

Peptides from syndecan 1 and methods of use therefor are described. These peptides can inhibit very late antigen-4 (VLA-4) interaction with vascular endothelial growth factor-2 (VEGFR2), thereby preventing tumor cell growth and tissue invasion.

11 Claims, 10 Drawing Sheets

Specification includes a Sequence Listing.

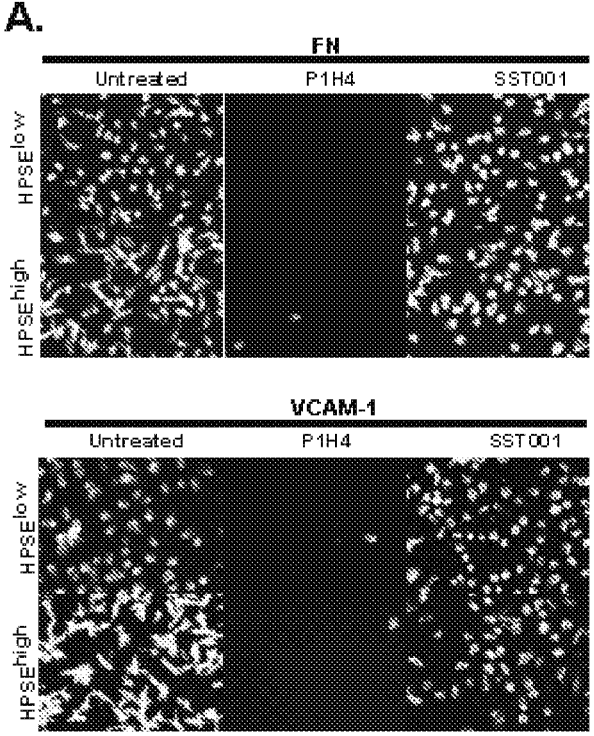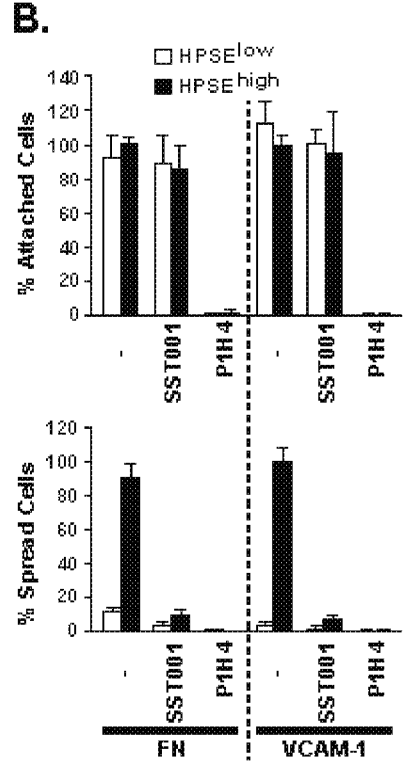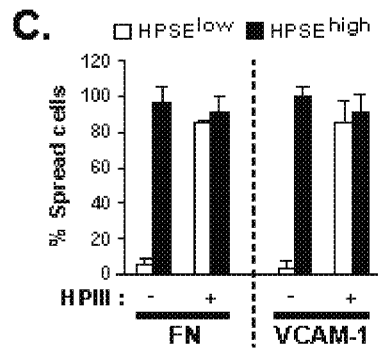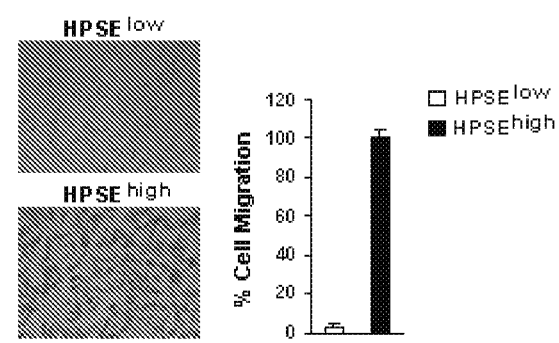
FIGS. 1A-D

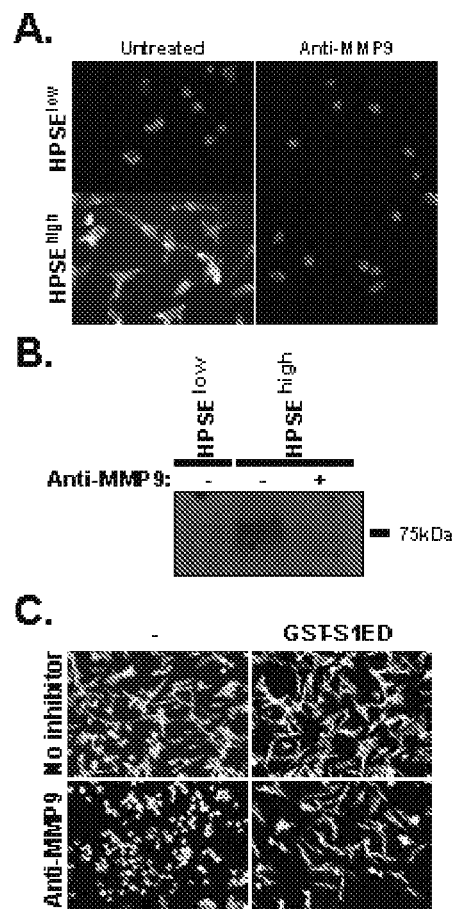
FIGS. 2A-C

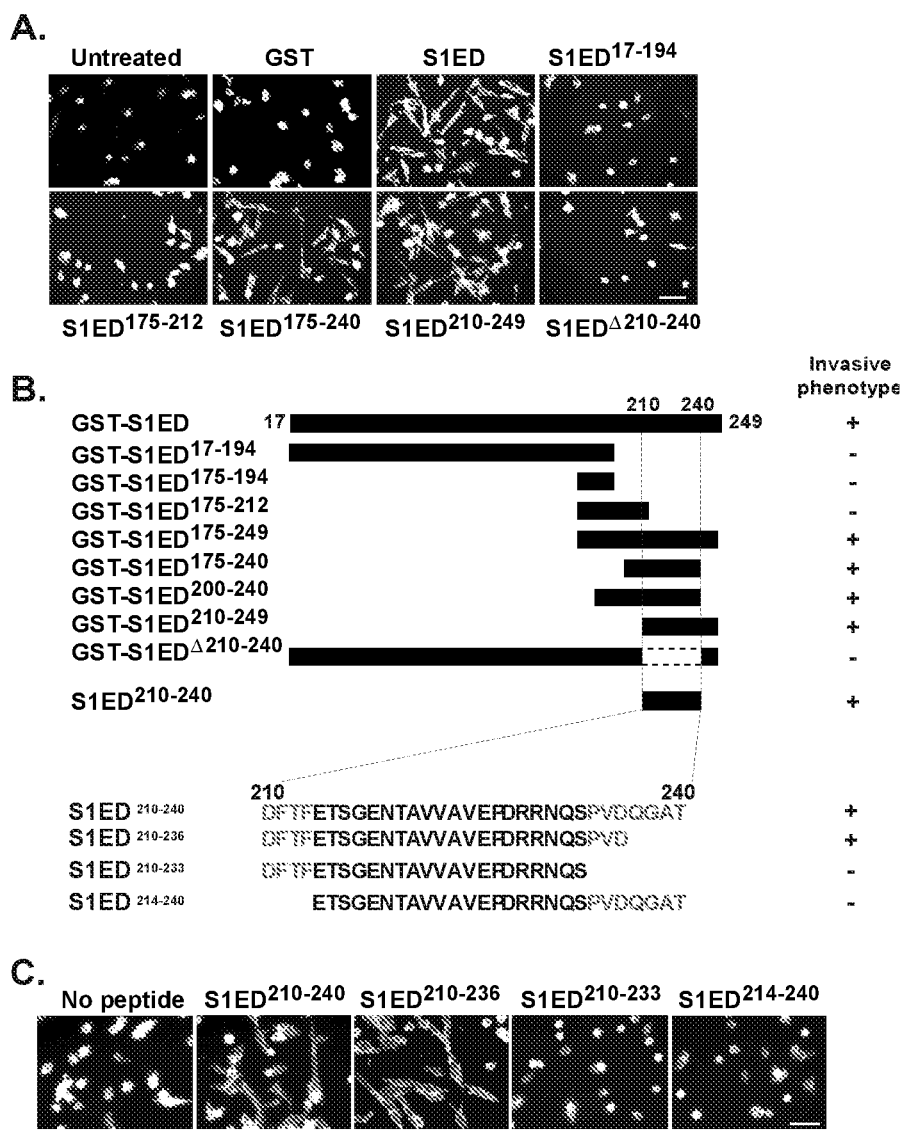
FIGS. 3A-C

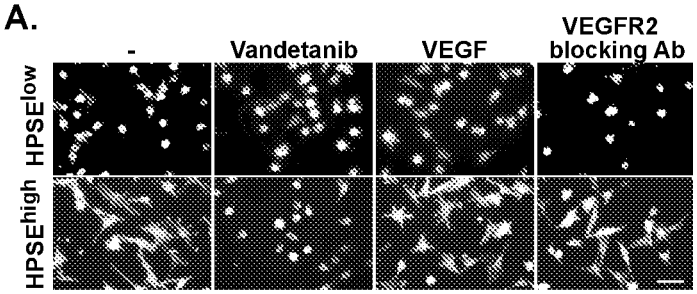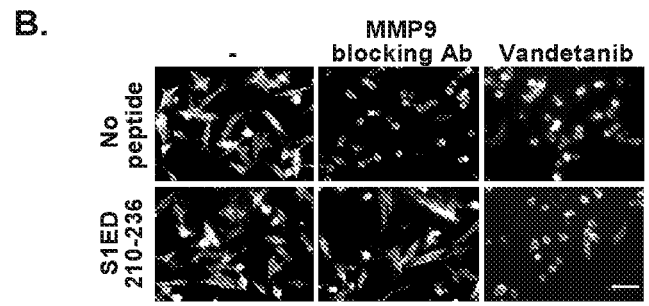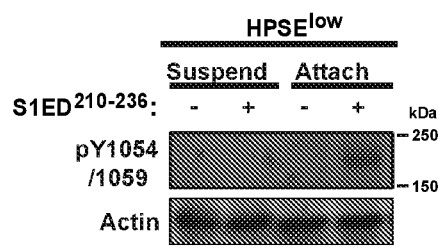
FIGS. 4A-C

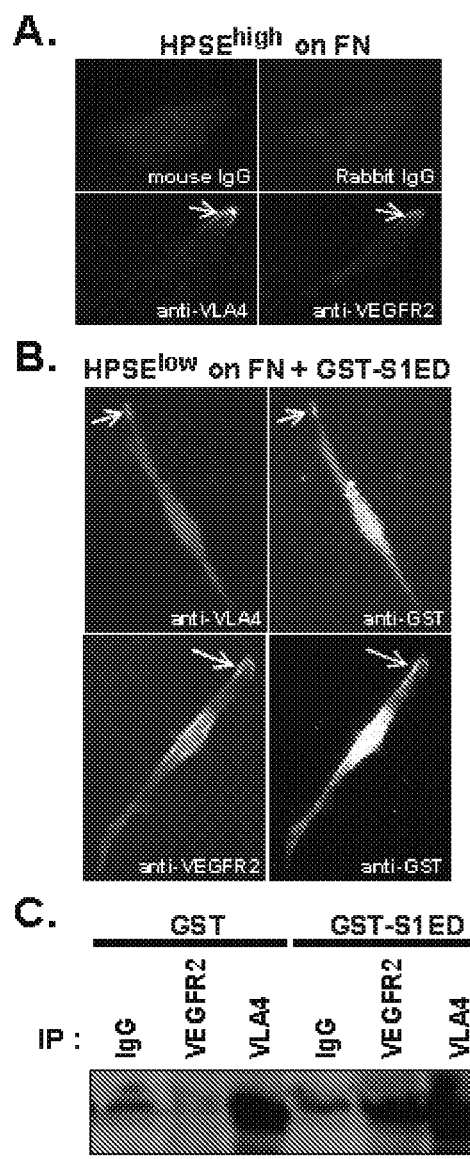
FIGS. 5A-C

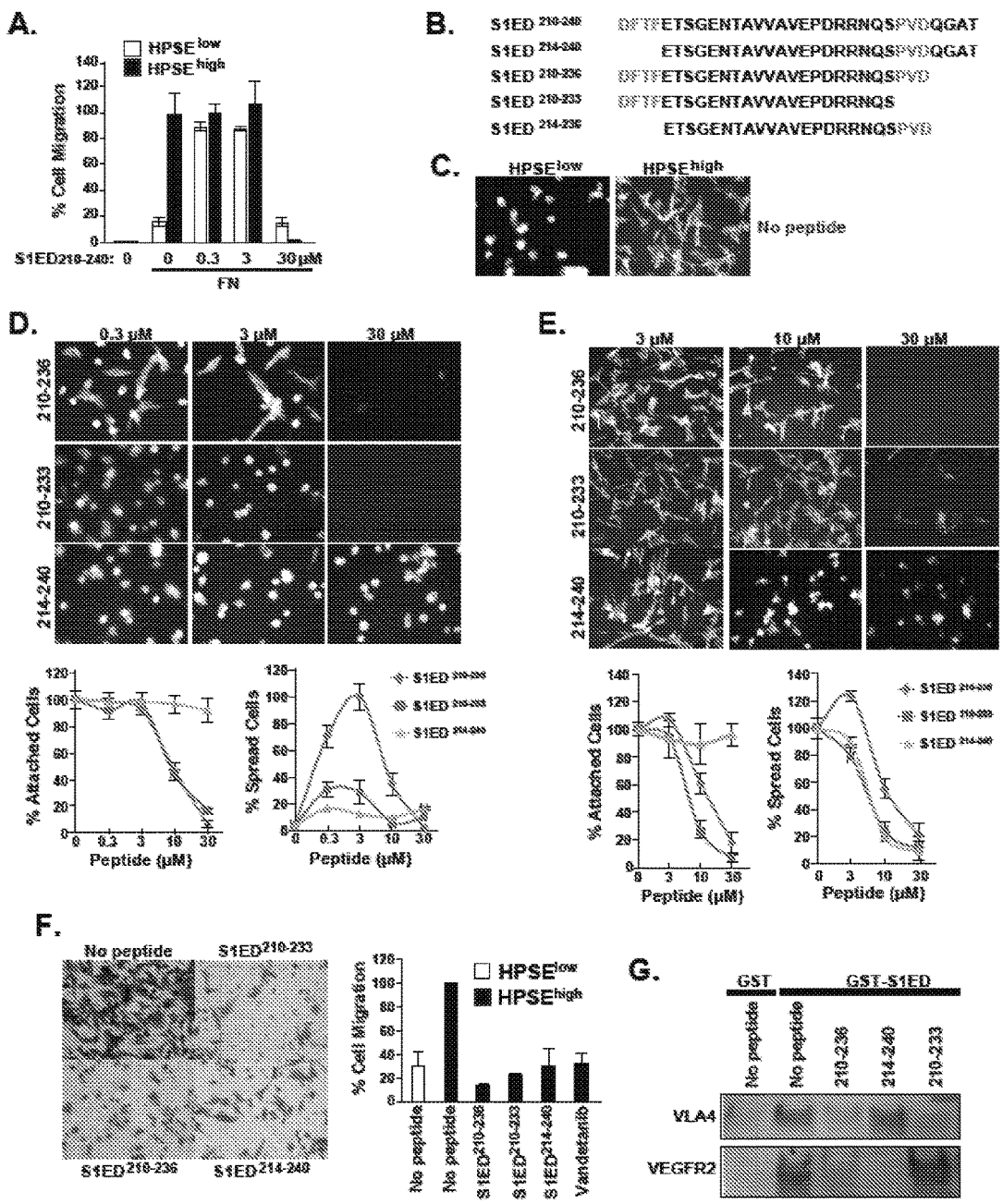
FIGS. 6A-G

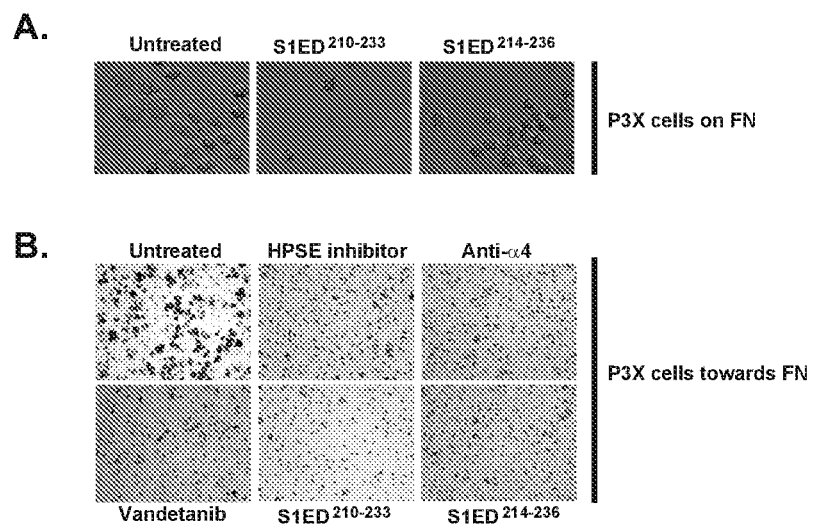
FIGS. 7A-B

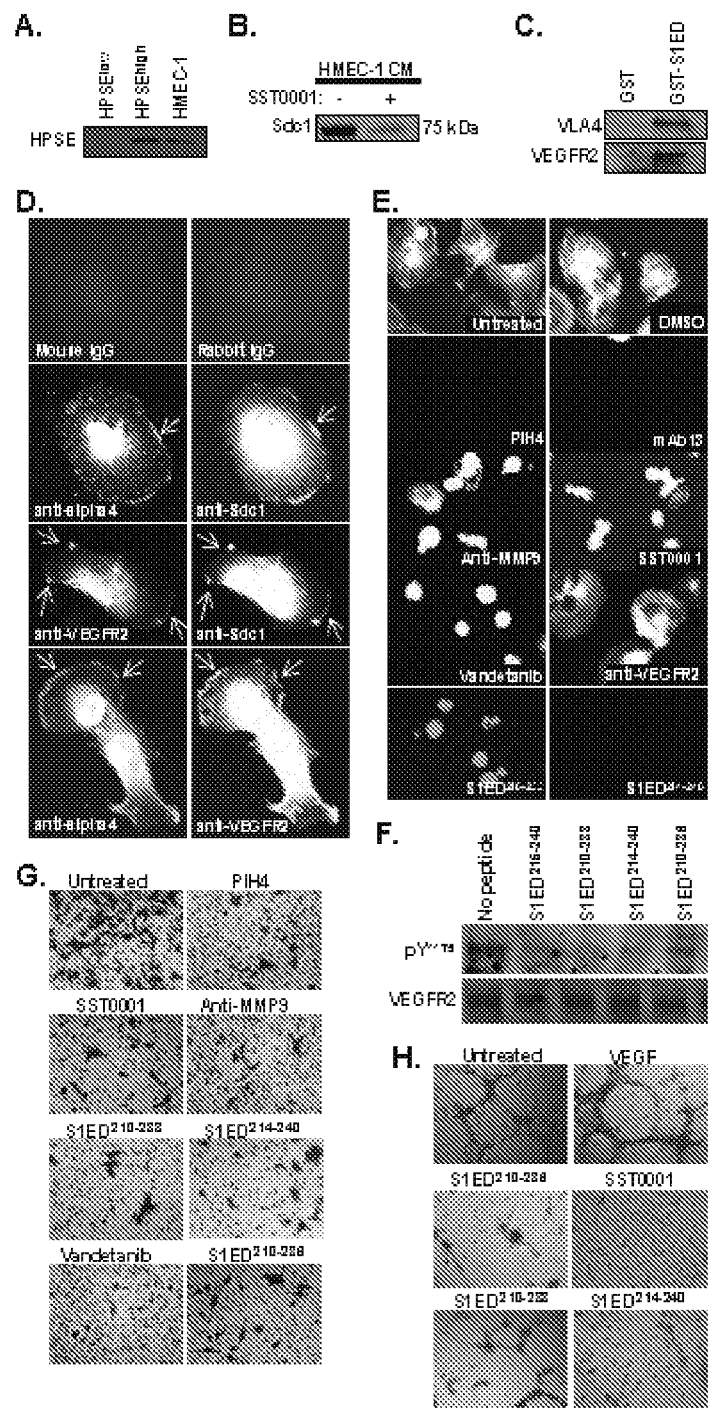
FIGS. 8A-H

HUMAN SYNDECAN-1 SEQUENCES

```
  1  mrraalwlwl calalslqpa lpqivatnlp pedgdgsgdd sdnfsgsgag alqditlsqq
 61  tpstwkdtql ltaiptspep tgleataast stlpagegpk egeavvlpev epgltareqe
121  atprprettq lptthqastt tattaqepat shphrdmqpg hhetstpagp sqadlhtpht
181  edggpsater aaedgassql paaegsgeqd ftfetsgent avvavepdrr nqspvdqgat
241  gasglldrk evlggviagg lvglifavcl vgfmlyrmkk kdegsyslee pkqanggayq
301  kptkqeefya (SEQ ID NO: 1)
```

210-240  DFTFETSGENTAVVAVEPDRRNQSPVDQGAT  (SEQ ID NO: 3)

210-236  DFTFETSGENTAVVAVEPDRRNQSPVD  (SEQ ID NO: 2)

210-233  DFTFETSGENTAVVAVEPDRRNQS  (SEQ ID NO: 4)

214-240  ETSGENTAVVAVEPDRRNQSPVDQGAT  (SEQ ID NO: 5)

220-236  TAVVAVEPDRRNQSPVD  (SEQ ID NO: 6)

214-236  ETSGENTAVVAVEPDRRNQSPVD  (SEQ ID NO: 7)

210-221  DFTFETSGENTA  (SEQ ID NO: 8)

FIG. 10

SEQUENCE LISTING

<160> NUMBER OF SEQ ID NOS: 8

<210> SEQ ID NO 1
<211> LENGTH: 310
<212> TYPE: PRT
<213> ORGANISM: Artificial Sequence
<220> FEATURE:
<223> OTHER INFORMATION: Synthetic Peptide

<400> SEQUENCE: 1

```
Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125
```

```
Thr Gln Leu Pro Thr Thr His Gln Ala Ser Thr Thr Ala Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 2
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 2

Asp Phe Thr Phe Glu Thr Ser Gly Glu Asn Thr Ala Val Val Ala Val
1               5                   10                  15

Glu Pro Asp Arg Arg Asn Gln Ser Pro Val Asp
            20                  25

<210> SEQ ID NO 3
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 3

Asp Phe Thr Phe Glu Thr Ser Gly Glu Asn Thr Ala Val Val Ala Val
1               5                   10                  15

Glu Pro Asp Arg Arg Asn Gln Ser Pro Val Asp Gln Gly Ala Thr
            20                  25                  30

<210> SEQ ID NO 4
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 4
```

```
Asp Phe Thr Phe Glu Thr Ser Gly Glu Asn Thr Ala Val Val Ala Val
1               5                   10                  15

Glu Pro Asp Arg Arg Asn Gln Ser
            20

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 5

Glu Thr Ser Gly Glu Asn Thr Ala Val Val Ala Val Glu Pro Asp Arg
1               5                   10                  15

Arg Asn Gln Ser Pro Val Asp Gln Gly Ala Thr
            20                  25

<210> SEQ ID NO 6
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 6

Thr Ala Val Val Ala Val Glu Pro Asp Arg Arg Asn Gln Ser Pro Val
1               5                   10                  15

Asp

<210> SEQ ID NO 7
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 7

Glu Thr Ser Gly Glu Asn Thr Ala Val Val Ala Val Glu Pro Asp Arg
1               5                   10                  15

Arg Asn Gln Ser Pro Val Asp
            20

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Asp Phe Thr Phe Glu Thr Ser Gly Glu Asn Thr Ala
1               5                   10
```

SYNDECAN PEPTIDES AND POLYPEPTIDES AS INHIBITORS OF VASCULAR ENDOTHELIAL GROWTH FACTOR RECEPTOR-2 (VEGFR2) AND VERY LATE ANTIGEN-4 (VLA-4)

CROSS-REFERENCE TO RELATED APPLICATIONS

This application is a divisional of U.S. application Ser. No. 15/043,951, filed on Feb. 15, 2016 and issued as U.S. Pat. No. 9,878,007 on Jan. 30, 2018, which claims the benefit of U.S. Provisional Patent Application No. 62/119,466, filed on Feb. 23, 2015. Each of these applications is incorporated by reference herein in its entirety.

STATEMENT REGARDING FEDERALLY SPONSORED RESEARCH OR DEVELOPMENT

This invention was made with government support under CA139872 awarded by the National Institutes of Health. The government has certain rights in the invention.

BACKGROUND

I. Field

This disclosure relates to regulation of cell growth, and more particularly to regulation of cancer cell growth. In particular, peptides and polypeptides derived from particular regions of Syndecan 1 have been shown to inhibit activation of VLA-4 ($\alpha 4\beta 1$ integrin) and engagement of VLA-4 by VEGFR2, thereby limiting tissue invasion.

2. Related Art

Multiple myeloma, a disease in which malignant plasma cells form disruptive bone tumors, is the second most prevalent hematologic malignancy in the United States (Laubach et al., 2010). The emergence of new therapies (e.g., bortezomib, thalidomide) has greatly improved survival rates in patients with myeloma (Laubach et al., 2010). However, these therapies slow rather than cure the disease and patients develop resistance and become refractory over the course of treatment. Thus, the need for novel therapies that prevent the progression of the disease and maintain patient quality of life remains a high priority. A better understanding of the mechanisms involved in disease progression may identify new and effective targets for such therapies.

Heparanase (HPSE), an endo-$\beta$-D-glucuronidase that degrades heparan sulfate (HS) chains on proteoglycans, is a tumor promoter in multiple myeloma, as well as in many other cancers (Barash et al., 2010, Kelly et al., 2003 and Vlodavsky et al., 2002). HPSE cleaves at highly specific sites within HS chains, releasing biologically active fragments 5 to 7 kDa in size that bind and promote the activity of heparin-binding growth factors. However, HPSE has far-reaching effects beyond the release of HS fragments, including altering the expression of genes that affect the proliferation, invasion and survival of tumor cells and other cells in the tumor microenvironment (Vlodavsky et al., 2002 and Levy-Adam et al., 2010). A major target of HPSE in multiple myeloma is syndecan-1 (Sdc1, CD138), one of a family of cell surface heparan sulfate proteoglycans found on most cells. Sdc1 is highly expressed on malignant plasma cells and has a causal role in multiple myeloma (Khotskaya et al., 2009; O'Connell et al., 2004; Sanderson and Yang, 2008 and Yang et al., 2002). Cells expressing high levels of Sdc1 exhibit enhanced invasion into collagen gels in vitro and as tumors in vivo (Yang et al., 2002). In contrast, suppression of Sdc1 expression causes apoptosis in myeloma cells (Khotskaya et al., 2009 and Wu et al., 2012).

Induction of metalloproteinase-9 (MMP-9) expression by HPSE, along with its pruning of the HS chains on Sdc1, causes MMP-9-mediated shedding of Sdc1 ectodomain into the tumor microenvironment where the proteoglycan enhances angiogenesis and is likely to have roles in myeloma cell adhesion, proliferation and survival (Yang et al., 2007; Mahtouk et al., 2007; Purushothaman et al., 2008 and Purushothaman et al., 2010). (Ramani et al., *JBC,* 287: 9952-9961 (2012). Indeed, high levels of shed Sdc1 in serum correlate with poor prognosis in multiple myeloma (Seidel et al., 2000 and Scudla et al., 2010). Although Sdc1 is shed, the steady-state level of functional Sdc1 at the cell surface remains unchanged due to an HPSE-induced increase in receptor expression (Yang et al., 2007; Mahtouk et al., 2007 and Ramani et al., 2012). Thus, the Sdc1 exists in at least two functional states in myeloma—a cell surface receptor and a bioactive agent in the extracellular milieu— and understanding its roles in these states appear highly critical for understanding the causes of highly malignant myeloma.

As a cell surface receptor, Sdc1 has an emerging role as an organizer of integrin and growth factor receptor signaling. The best-characterized example involves the insulin-like growth factor-1 receptor (IGF-1R) and the $\alpha v \beta 3$- or $\alpha v \beta 5$-integrin. These receptors are captured by an active site in the extracellular domain of Sdc1 (aa 92-119 in mouse Sdc1, 93-120 in human Sdc1); their capture by Sdc1 at sites of matrix adhesion promotes activation of the IGF-1R, which generates an inside-out signal that activates the integrins (Beauvais et al., 2009; Beauvais and Rapraeger, 2010; and McQuade et al., 2006). A peptide that mimics the active site in human Sdc1 (synstatin 93-120, also called $SSTN_{IGF1R}$) disrupts the assembly of this complex on tumor cells and activated vascular endothelial cells, blocks tumor growth and tumor-induced angiogenesis, and is a candidate for therapeutic intervention in human disease. These findings suggest that Sdc1, either as a cell surface receptor, or when shed from the cell surface, has a role in activating receptor tyrosine kinases and/or integrins.

VLA-4 (very late antigen-4, or the $\alpha 4\beta 1$ integrin) participates in the infiltration of leucocytes and lymphocytes (Alon and Feigelson, 2002; Alon et al., 1995). In addition to using VLA-4 for extravasation from the blood stream, myeloma cells rely on VLA-4 to engage bone marrow stromal cells, and fibronectin (FN) in the marrow extracellular matrix (ECM) for growth and survival (Sanz-Rodriguez et al., 1999; Vande Broek et al., 2008) and to resist therapeutic drugs (Noborio et al., 2009) (e.g., "cell adhesion-mediated drug resistance (CAM-DR)" (Meads et al., 2008; Damiano et al., 2000; Damiano et al., 1999; Schmidmaier et al., 2006). Binding to VCAM-1 on marrow stromal cells also causes release of MIP-1$\alpha$ and MIP-1$\beta$, activating osteoclasts and bone erosion (Abe et al., 2009; Michigami et al., 2000).

Angiogenesis and lymphangiogenesis also play important roles in tumor growth and metastasis by providing nutrients exchange as well as avenues for tumor cell extravasation, including in hematological malignancies (Orpana and Salven, 2002). VLA-4 expression is required for angiogenesis by both vascular and lymphatic endothelial cells and its activity is especially prominent in tumors (Garmy-Susini et al., 2013; 2010; 2005). Its matrix ligand, FN, is deposited within the growing vascular and lymphatic microvessels and VCAM-1 is prominently expressed on mural cells (pericytes) that support vascular endothelial cells.

Vascular endothelial cells also rely on vascular endothelial growth factor receptor-2 (VEGFR2) and this receptor tyrosine kinase is often aberrantly expressed in many tumors as well, including in multiple myeloma (Kumar et al., 2003 and Ria et al., 2003). VEGFR2 inhibitors have been shown to block proliferation and migration of patient-derived myeloma cells (Martinelli et al., 2001). Bone marrow angiogenesis involving VEGFR2 also plays an important role in the progression of multiple myeloma as in other hematological malignancies (Rajkumar et al., 2000; Vacca et al., 1994 and Rajkumar et al., 2002). Interestingly, Sdc1 extracellular domain shed from myeloma cells expressing high levels of HPSE has been shown to promote VEGF-dependent angiogenesis in vitro. This depends on its HS chains, but also on its core protein, suggesting the presence of one or more active sites responsible for the bioactivity of the shed Sdc1.

SUMMARY

Thus, in accordance with the present disclosure, there is provided an isolated and purified peptide segment consisting of between 12 and 100 amino acid residues and comprising residues 210-221, 220-236, 210-233, 210-236, 214-236 or 214-240 of SEQ ID NO:1. The peptide may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The peptide may be between 12 and 50 amino acid residues in length. The peptide may be between 23 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The peptide may comprise residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The peptide may consist of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3).

In another embodiment, there is provided a nucleic acid encoding a peptide segment consisting of between 12 and 100 amino acid residues and comprising residues 210-221, 220-236, 210-233, 210-236, 214-236 or 214-240 of SEQ ID NO:1. The nucleic acid may encode a peptide of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The nucleic acid may encode a peptide of between 12 and 50 amino acid residues in length. The peptide may be between 23 and 50 amino acid residues in length. The nucleic acid may encode a peptide of between 16 and 30 amino acid residues in length. The nucleic acid may encode a peptide of between 23 and 27 amino acid residues in length. The nucleic acid may encode a peptide consisting essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The nucleic acid may encode a peptide comprising residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The nucleic acid may encode a peptide consisting of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3).

In yet another embodiment, there is provided a method of inhibiting α4β1 integrin (VLA-4) interaction with VEGFR2 comprising contacting a VEGFR2 molecule with a peptide segment consisting of between 12 and 100 amino acid residues and comprising 210-221, 220-236, 210-233, 210-236, 214-236 or 214-240 of SEQ ID NO:1. The peptide or polypeptide may be 12, 13, 14, 15, 16, 17, 18, 19, 20, 21, 22, 23, 24, 25, 26, 27, 28, 29, 30, 31, 35, 40, 45, 49, 50, 55, 60, 65, 70, 75, 80, 85, 90, 95 or 100 amino acid residues in length. The peptide may be between 12 and 50 amino acid residues in length. The peptide may be between 23 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The peptide may comprise residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The peptide may consist of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The α4β1 integrin (VLA-4) and/or VEGFR2 may be located on the surface of a cell, such as a lymphoid cell, including a plasma cell, or a vascular endothelial cell or a lymphatic endothelial cell. The cell may also be a cancer cell, such as a carcinoma, a myeloma (including multiple myeloma), a leukemia (including CLL), a lymphoma, a melanoma, a schwannoma, a malignant peripheral nerve sheath tumor cell, a malignant endothelial cell or a glioma. The method may further comprise contacting said cancer cell with a second cancer inhibitory agent. The cancer cell may be a metastatic cancer cell or tumor stem cell. The step of contacting may comprise providing to said cell an expression construct comprising a nucleic acid encoding a peptide segment consisting of between 12 and 100 amino acid residues and comprising residues 210-221, 210-233, 210-236 or 214-236 or 214-240 of SEQ ID NO:1 operably linked to a promoter active in said cell.

In yet another embodiment, there is provided a method of inhibiting α4β1 integrin (VLA-4) interaction with syndecan-1 comprising contacting a syndecan-1 molecule with a peptide segment consisting of between 12 and 100 amino acid residues and comprising 210-221, 210-233, 210-236, or 210-240 of SEQ ID NO:1. The peptide or polypeptide may be 12, 13, 14, 15, 16, 17, 18, 19, 20, 21, 22, 23, 24, 25, 26, 27, 28, 29, 30, 31, 35, 40, 45, 49, 50, 55, 60, 65, 70, 75, 80, 85, 90, 95 or 100 amino acid residues in length. The peptide may be between 12 and 50 amino acid residues in length. The peptide may be between 14 and 50 amino acid residues, 23 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), or residues 210-240 (SEQ ID NO:

3). The peptide may comprise residues 210-221 (SEQ ID NO: 8), 210-233 (SEQ ID NO: 4), 210-236 (SEQ ID NO: 2), or 210-240 (SEQ ID NO: 3). The peptide may consist of residues 210-221 (SEQ ID NO: 8), 210-233 (SEQ ID NO: 4), 210-236 (SEQ ID NO: 2), or 210-240 (SEQ ID NO: 3). The α4β1 integrin (VLA-4) and/or syndecan-1 may be located on the surface of a cell, such as a lymphoid cell, including a plasma cell, or a vascular endothelial cell or a lymphatic endothelial cell. The cell may also be a cancer cell, such as a carcinoma, a myeloma (including multiple myeloma), a leukemia (including CLL), a lymphoma, a melanoma, a schwannoma, a malignant peripheral nerve sheath tumor cell, a malignant endothelial cell or a glioma. The method may further comprise contacting said cancer cell with a second cancer inhibitory agent. The cancer cell may be a metastatic cancer cell or tumor stem cell. The step of contacting may comprise providing to said cell an expression construct comprising a nucleic acid encoding a peptide segment consisting of between 24 and 100 amino acid residues and comprising residues 210-221, 210-233, 210-236 or 210-240 of SEQ ID NO: 1 operably linked to a promoter active in said cell.

In still yet a further embodiment, there is provided a method of screening for an agent that inhibits the binding of syndecan-1 and either VLA-4 or VEGFR2 comprising (a) providing a syndecan-1 or a fragment thereof and VLA-4 or VEGFR2, or fragments thereof, wherein said syndecan-1 or a fragment thereof and VLA-4 or VEGFR2, or fragments thereof are capable of binding each other; (b) contacting the proteins or fragments of step (a) with a candidate substance; and (c) assessing the binding of said syndecan-1 or a fragment thereof and VLA-4 or VEGFR2, or fragments thereof, wherein reduced binding in step (c) as compared to the binding in the absence of said candidate substance identifies said candidate substance as an agent that inhibits the binding of syndecan-1 and VLA-4 or VEGFR2, or fragments thereof. The candidate substance may be a protein, a peptide, a peptidometic, a polynucleotide, an oligonucleotide, or a small molecule. One or both of said syndecan-1 or a fragment thereof and VLA-4 or VEGFR2, or fragments thereof may be labeled with a detectable label. Step (c) may comprise FRET, immunodetection, a gel-shift assay, or a phosphorylation assay. The candidate substance may be a peptide segment consisting of between 20 and 100 amino acid residues and comprising residues 210-221, 210-233, 210-236, 214-236 or 214-240 of SEQ ID NO: 1. Step (a) may further comprise including VLA-4 or a fragment thereof that interacts with syndecan-1 and/or VLA-4 and/or VEGFR2, or fragments thereof. The method may further comprise a control reaction of assessing the binding of said syndecan-1 or a fragment thereof and said VEGFR2 or a fragment thereof in the absence of said candidate substance. Steps (a)-(c) may be performed in a cell-free system, performed in a cell or performed in vivo.

In a further embodiment, there is provided a method of treating a subject with a cancer, cancer cells of which express VLA-4 and/or VEGFR2, comprising contacting said cells with a peptide segment consisting of between 12 and 100 amino acid residues and comprising residues 210-221, 220-236, 210-233, 210-236, 214-236 or 214-240 of SEQ ID NO: 1. The peptide may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The peptide may be between 12 and 50 amino acid residues in length. The peptide may be between 23 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The peptide may comprise residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The peptide may consist of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The subject may be a human or a non-human mammal. The cancer may be a carcinoma, a leukemia (including CLL), a lymphoma, a myeloma (including multiple myeloma), a melanoma or a glioma. The peptide may be administered directly to said cancer cells, local to said cancer cells, regional to said cancer cells, or systemically. The method may further comprise administering to said subject a second cancer therapy selected from chemotherapy, radiotherapy, immunotherapy, hormonal therapy, or gene therapy. The method may further comprise administering said peptide to said subject more than once.

In yet a further embodiment, there is provided a method of inhibiting pathologic scarring or wound repair in a subject to comprising administering to said subject a peptide segment consisting of between 12 and 100 amino acid residues and comprising resides 210-221, 220-236, 210-233, 210-236, 214-236 or 214-240 of SEQ ID NO:1. The peptide or polypeptide may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The peptide may be between 12 and 50 amino acid residues in length. The peptide may be between 23 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The peptide may comprise residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The peptide may consist of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3).

In still yet a further embodiment, there is provided a method of inhibiting pathologic neovascularization or lymphangiogenesis comprising administering to said subject a peptide segment consisting of between 12 and 100 amino acid residues and comprising residues 210-221, 220-236, 210-233, 236, 214-236 or 214-240 of SEQ ID NO: 1. The peptide or polypeptide may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The peptide may be between 16 and 50 amino acid residues in length. The peptide may be between 12 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The peptide may comprise residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The peptide may consist of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The pathological neovascularization may involve activated vascular endothelial cells.

In an additional embodiment, there is provided a method of promoting wound healing comprising contacting an injured tissue site with syndecan-1 or an active fragment thereof. The injured tissue site may be a surgery site, a trauma site, or a site of hypoxic injury. The site of hypoxic injury is infarcted myocardium. The syndecan-1 fragment may comprise residues 210-236 (SEQ ID NO: 2) or 210-240 (SEQ ID NO: 3).

Another embodiment comprises a method of treating an inflammatory or autoimmune disease or immune rejection of transplanted organs comprising administering to a subject a peptide segment consisting of between 12 and 100 amino acid residues and comprising resides 210-221, 220-236, 210-233, 210-236, 214-236 or 214-240 of SEQ ID NO: 1. The disease may be rheumatoid arthritics, inflammatory bowel disease, Crohn's disease, multiple sclerosis, or systemic lupus erythematosus. Administering may comprise systemic administration or administration local or regional to an affected disease site. The peptide or polypeptide may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The peptide may be between 16 and 50 amino acid residues in length. The peptide may be between 12 and 50 amino acid residues in length. The peptide may be between 16 and 30 amino acid residues in length. The peptide may be between 23 and 27 amino acid residues in length. The peptide may consist essentially of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or residues 210-240 (SEQ ID NO: 3). The peptide may comprise residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3). The peptide may consist of residues 210-221 (SEQ ID NO: 8), 210-233 (SEQ ID NO: 4), 210-236 (SEQ ID NO: 2), 214-236 (SEQ ID NO: 7) or 214-240 (SEQ ID NO: 5), or 210-240 (SEQ ID NO: 3).

It is contemplated that any method or composition described herein can be implemented with respect to any other method or composition described herein.

Consisting essentially thereof, as used herein, means that the peptide contains other elements that do not substantially alter the function of the peptide without that element.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed.

FIGS. 1A-D. Adhesion of CAG cells to FN or VCAM-1 by α4β1-integrin is enhanced by HPSE leading to cell spreading and migration. (FIG. 1A) HPSE$^{low}$ or HPSE$^{high}$ cells were plated on FN or VCAM-1 for 2.5 hr with or without treatment of HPSE inhibitor SST0001 or 10 μg/ml α4 blocking antibody (clone P1H4) and stained with fluorescent phalloidin. CAG cells expressing low or high levels of HPSE were treated with 500 μg/ml of the HPSE inhibitor SST0001 for 24 hr prior to plating. (FIG. 1B) Quantification of HPSE$^{low}$ and HPSE$^{high}$ cells attachment and spreading on 40 μg/ml FN or 5 μg/ml VCAM-1 in the presence or absence of HPSE inhibitor SST0001 and 10 μg/ml α4 blocking antibody. (FIG. 1C) HPSE$^{low}$ and HPSE$^{high}$ cells were pretreated with heparinase III for 2.5 hrs and then plated on FN and VCAM-1. (FIG. 1D) Transwell migration assays towards FN (for 12 hrs) were performed with HPSE$^{low}$ and HPSE$^{high}$ cells. Cell migrating to the bottom-side of the filter were counted in five random images for each experiment. Error bars represented S.D.

FIGS. 2A-C. MMP-9-mediated shedding of Sdc1 is necessary for the HPSE-enhanced effect in CAG cells. (FIG. 2A) HPSE$^{low}$ and HPSE$^{high}$ cells were plated on VCAM-1 for 2.5 hrs in the absence or presence of 10 μg/ml MMP9 blocking antibody and stained with fluorescent phalloidin. (FIG. 2B) HPSE$^{low}$ and HPSE$^{high}$ cells were seeded at equal density and grown in serum-free media for 2.5 hr in the absence or presence of 20 μg/ml MMP9 blocking antibody. After 2.5 hr, conditioned media were harvested, and the level of shed Sdc1 in the conditioned medium from each condition was determined by immunoblotting following heparinase digestion. (FIG. 2C) HPSE$^{high}$ cells were plated on FN in the absence or presence of 10 μg/ml MMP blocking antibody with or without treatment with GST-S1ED.

FIGS. 3A-C. Amino acids 210-236 in the Sdc1 ectodomain can mimic the effects of HPSE. (FIG. 3A) HPSE$^{low}$ cells were plated on VCAM-1 and treated with 4 μM GST-S1ED constructs shown (Bar=50 μm); (FIG. 3B) Schematic presentation of GST-tagged S1ED constructs and S1ED peptides used and a summary of their ability to induce spreading indicative of the invasive phenotype; (FIG. 3C) HPSE$^{low}$ cells were plated on VCAM-1 in the absence or presence of 0.3 μM S1ED$^{210-240}$, S1ED$^{210-236}$, S1ED$^{210-233}$ or S1ED$^{214-240}$ peptide. (Bar=50 μm). Sequences in FIG. 3C are 210-240 (SEQ ID NO: 3), 210-236 (SEQ ID NO: 2), 210-233 (SEQ ID NO: 4) and 214-240 (SEQ ID NO: 5).

FIGS. 4A-C. HPSE expression leads to activation of VEGFR2 when α4-integrin engages ligand. (FIG. 4A) HPSE$^{low}$ and HPSE$^{high}$ cells treated with or without 1 μM Vandetanib, 20 ng/ml VEGF, or 20 μg/ml VEGFR2 blocking antibody are plated on VCAM-1 to observe cell spreading (Bar=50 μm); (FIG. 4B) HPSE$^{high}$ cells plated on FN were treated with MMP-9 blocking antibody or 1 μM Vandetanib in the absence or presence of 0.3 μM S1ED$^{210-236}$ (Bar=50 μm); (FIG. 4C) HPSE$^{low}$ cells were kept in suspension or were seeded on FN in the absence or presence of 0.3 µM S1ED$^{210-236}$ for 2.5 h. Cell lysates were immunoblotted with antibodies against pY1054/1059 in VEGFR2 as a marker of VEGFR2 activation. Actin is shown as a loading control.

FIGS. 5A-C. Recombinant Sdc1 ectodomain (GST-S1ED) causes capture of VEGFR2 by VLA-4. (FIG. 5A) HPSE$^{high}$ cells were plated on FN for 2.5 hrs and double stained for VLA-4 and VEGFR2. (FIG. 5B) HPSE$^{low}$ cells were plated on FN in the presence of 4 µM GST-S1ED. After 2.5 hrs, cells were double-stained for GST to detect the GST-S1ED and VLA-4 or VEGFR2. (FIG. 5C) HPSE$^{low}$ cells were plated on FN-pre-coated dishes for 2.5 hr in the absence or presence of GST-S1ED and whole cell lysates were prepared for immunoprecipitation with anti-VEGFR2 and VLA-4 antibodies. The associated VLA-4 was detected by immunoblotting with a VLA-4 antibody.

FIGS. 6A-G. Peptides derived from the active site in Sdc1 activate or inhibit adhesion and invasion. (FIG. 6A) Transwell migration assays towards FN (for 16 hrs) were performed for HPSE low or high cells in the presence of 0, 0.3, 3, and 30 µM of S1ED$^{210-240}$. Cells migrating to the bottom side of the filter were counted from five random images for each treatment. (FIG. 6B) The sequence of S1ED$^{210-240}$ is shown (SEQ ID NO: 3), as well as three truncation mutants of the peptide (SEQ ID NOs: 5, 2, 4 and 7). Amino acids shown in red appear necessary for the spreading and invasive activity. (FIG. 6C) Images of HPSE$^{low}$ and HPSE$^{high}$ cells plated on FN for 2 hr. (FIG. 6D) HPSE$^{low}$ cells were treated with 0, 0.3, 3, 10 and 30 µM of S1ED$^{210-236}$, S1ED$^{210-233}$, or S1ED$^{214-240}$, plated on FN for 2 hr, fixed and stained with fluorescent phalloidin. Cells from five random images were quantified for cell attachment and cell spreading. (FIG. 6E) HPSE$^{high}$ cells were treated with 0, 3, 10, and 30 µM of S1ED$^{210-236}$, S1ED$^{210-233}$, and S1ED$^{214-240}$, plated on FN for 2 hr, then fixed, imaged and quantified as in FIG. 6D. (FIG. 6F) Transwell migration assays towards FN (for 16 hr) were performed for HPSE low or HPSE$^{high}$ cells in the presence of 30 µM of S1ED$^{210-236}$, S1ED$^{210-233}$, S1ED$^{214-240}$ and Vandetanib. (FIG. 6G) HPSE$^{low}$ cell lysates were incubated overnight with glutathione beads coated with GST or GST-S1ED in the absence or presence of 30 µM of S1ED$^{210-236}$, S1ED$^{210-233}$, and S1ED$^{214-240}$ Capture of VLA-4 or VEGFR2 was detected by immunoblotting. Sequences in FIG. 6B are 210-240 (SEQ ID NO: 3), 210-236 (SEQ ID NO: 2), 210-233 (SEQ ID NO: 4), 214-240 (SEQ ID NO: 5) and 214-236 (SEQ ID NO: 7).

FIG. 7A-B. S1ED$^{214-236}$, specific for VEGFR2 coupling to VLA-4, blocks myeloma cell invasion but not adhesion. (FIG. 7A) P3×63Ag8 mouse myeloma cells are plating on the VLA-4 ligand FN in the presence or absence of 30 uM S1ED$^{210-233}$ (SEQ ID No: 4) or S1ED$^{214-236}$ (SEQ ID No: 7) for 2.5 hr. (FIG. 7B) P3×63Ag8 myeloma cells are plated on FN-coated filters in the presence of HPSE inhibitor OGT2115, VLA-4 blocking antibody P1H4, VEGFR2 inhibitor Vandetanib or S1ED$^{210-233}$ or S1ED$^{214-236}$ and allowed to migrate through the filter for 16 hr. Small black dots are the pores in the filter. Cell migration is only observed in the untreated controls.

FIGS. 8A-H. HPSE mediated the Sdc1-coupled VEGFR2 complex in endothelial cells induces angiogenesis. (FIG. 8A) Lysates from HPSE$^{low}$, HPSE$^{high}$ and HMEC-1 cells are probed by immunoblotting for expression of HPSE. (FIG. 8B) HMEC-1 cells were seeded at equal density and grown in serum-free media for 24 hr in the absence or presence of 125 µg/ml of the HPSE inhibitor SST0001. After 24 hr, conditioned media were harvested, and the level of shed Sdc1 in the conditioned medium from each condition was determined by immunoblotting. (FIG. 8C) HMEC-1 cell lysate was incubated overnight with glutathione beads coated with GST or GST-S1ED. Capture of VLA-4 or VEGFR2 was detected by immunoblotting. (FIG. 8D) HMEC-1 cells were plated on IIICS for 3 hr and double stained for VLA-4 and Sdc1, VEGFR2 and Sdc1, or VLA-4 and VEGFR2. (FIG. 8E) HMEC-1 cells were treated with DMSO, VLA-4 blocking antibody P1H4, β1-integrin blocking antibody mAb13, g/ml MMP9 blocking antibody, 125 µg/ml HPSE inhibitor SST0001, Vandetanib, VEGFR2 blocking antibody, 30 µM S1ED$^{210-233}$ or 30 µM S1ED$^{214-240}$ and then plated on IIICS. Images were taken from random field with 200× magnification for counting attached and spread cells. (FIG. 8F) HMEC-1 cells were plated on IIICS in the presence of 10 µM of S1ED$^{210-236}$, S1ED$^{210-233}$, S1ED$^{215-240}$, and S1ED$^{214-240}$. Lysates were probed on immunoblots with antibodies against pY$^{1175}$ VEGFR2 and VEGFR2. (FIG. 8G) Transwell migration assays towards IIICS (for 16 hr) were performed for HMEC-1 cells in the presence of P1H4, SST0001, Anti-MMP9, Vandetanib, S1ED$^{210-236}$, S1ED$^{210-233}$, and S1ED$^{214-240}$. Images were taken from random field with 200× magnification for counting migrated cells. (FIG. 8H) A 96-well plate coated with 50 µl Matrigel containing 100 µg/ml IIICS per well was solidified at 37° C. for 2 hrs. HMEC-1 cells (2.5×10$^4$ cells/well) were seeded into the plate and cultured in media containing VEGF, SST0001, 10 µM of S1ED$^{210-236}$, S1ED$^{210-233}$, S1ED$^{215-240}$, and S1ED$^{214-240}$ for 24 hrs. Enclosed capillary networks of tubes were taken from random field with 200× magnification.

FIG. 10. Human Syndecan-1 Sequences. Full length syndecan-1 sequences and relevant fragments are illustrated.

DESCRIPTION OF ILLUSTRATIVE EMBODIMENTS

Figure 9:
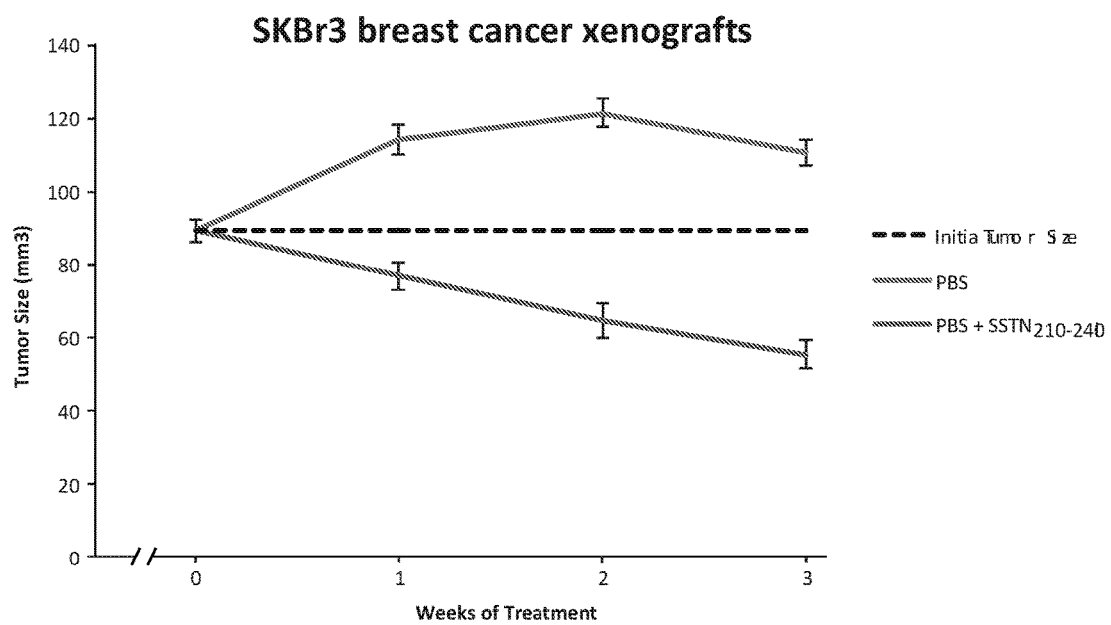
FIG. 9. Treatment of breast cancer xenograft with systemic S1ED$^{210-240}$. 4×10$^6$ human SKBr3 mammary carcinoma cells were injected in a 1:1 mix with matrigel into the posterior flanks of immunodeficient nude (nu/nu) mice and allowed to establish for one week as palpable tumors. Alzet pumps were then implanted subcutaneously on the anterior dorsal backs of the animals, systemically delivering either phosphate buffered-saline alone (PBS) or S1ED 210-240 peptide in PBS for 3 weeks of treatment. Peptide was delivered at 1.09 mg/kg/day, a concentration estimated to achieve concentrations sufficient to block the VLA-4/VEGFR2 mechanism. Tumor sizes were measured with calipers and converted to tumor volumes using the equation V=0.524× L× W. The data are shown as the mean of 12 tumors+/−S.E.M.

As discussed above, receptor tyrosine kinases and integrin play a major role in oncogenesis, often working together. A significant question that has remained unanswered is whether the activity of these two classes of receptors are jointly regulated, perhaps by a third "organizer" receptor. The inventors' laboratory has previously shown that syndecans appear to be the organizer. The focus here will be on Sdc1, which is expressed on epithelial cells (Bernfield et al., 1992; David et al., 1992), but also endothelial and myeloma cells (Beauvais et al., 2009; Sanderson and Bernfield, 1988; Liu et al., 1998). Previously, this molecule was shown to co-immunoprecipitate with the αvβ3 integrin and IGF-1R from breast carcinoma and activated endothelial cells (Beauvais et al., 2009; Beauvais et al., 2010). It captures the integrin and receptor tyrosine kinase via a site in its extracellular domain (amino acids 93-120 in human Sdc1) that is unique to this syndecan. Activation of the integrin and signaling by IGF-1R requires their capture by Sdc1, which the inventors report is disrupted by a peptide mimetic (called a "synstatin" or SSTN) of the active site (e.g., $SSTN_{IGF1R}$). More recently it has been shown that Sdc1 also co-immunoprecipitates with the α6β4 integrin, α3β1 integrin and HER2 from activated keratinocytes, A431 cervical carcinoma cells, breast carcinoma cells and HN squamous carcinoma cells (Wang et al., 2010; Wang et al., 2014; Wang et al., 2015). Whereas the 6034 integrin is captured by the syndecan cytoplasmic domain, HER2 and the α3β1 are captured by a site in the extracellular domain, that is distinct from the αvβ3/IGF-1R capture site. Importantly, HER2 docks only with Sdc1/α3β1 and not with the other syndecans. The interaction site capturing HER2/α3β1 is distinct from other syndecans, and the inventors' laboratory has reported that recombinant Sdc1 peptides mimicking this interaction site (designated as "synstatin-HER2" or "SSTN$_{HER2}$") block this interaction. Sdc1 binding its site in the β4 integrin cytoplasmic domain is essential for signaling by this complex, as mutation of this Sdc1-specific site generates a β4 dominant negative mutant (DNM) that specifically blocks the Sdc1-coupled signaling mechanism.

In the work described here, the inventors examine the role of HPSE on myeloma cell adhesion and a potential link to Sdc1 acting as an organizer of matrix- and growth factor-dependent signaling. They now show that human CAG myeloma cells bind via α4-integrin (also called "very late antigen-4" or VLA-4) to fibronectin (FN), an abundant bone marrow matrix ligand, and to vascular cell adhesion molecule-1 (VCAM-1), a receptor found on microvascular endothelial cells and on stromal cells within the bone marrow microenvironment[3, 4]. CAG cells expressing elevated levels of HPSE adopt an invasive phenotype, characterized by polarized spreading and directional cell migration on these ligands. The HPSE-induced phenotype depends on the shedding of Sdc1, which can be mimicked by addition of soluble recombinant Sdc1 ectodomain or a peptide (a.a. 210-236) that represents a novel active site in the syndecan extracellular domain. The phenotype also depends on activation of VEGFR2, although activation of VEGFR2 by its ligand, VEGF, rather than by Sdc1 does not cause the phenotype. Instead, Sdc1 couples VEGFR2 to VLA-4, which, when engaged and clustered by FN or VCAM-1, activates VEGFR2 and stimulates the invasive phenotype. Low concentrations of $S1ED^{210-236}$ stimulate the invasive phenotype, whereas higher concentration block the phenotype in CAG cells expressing high levels of HPSE. This behavior is typical of a peptide that has binding sites for two receptors, such that at low concentrations a single peptide bridges both receptors and couples them together, whereas at higher concentrations single peptides occupy the binding sites on individual receptors and prevent any single peptide from bridging and coupling them together. Analysis of binding sites within this peptide reveal that VLA-4 requires a binding site at the N-terminus (amino acids 210-213), whereas VEGFR2 requires amino acids near the C-terminus (amino acids 234-236). Peptides bearing only one of these binding sites bind only a single receptor and prevent endogenous Sdc1 from coupling the receptors together, thus acting as inhibitors. The peptide that engages only VLA-4 inactivates the integrin, completely blocking adhesion by the cells. The peptide that engages only VEGFR2 does not block adhesion, but blocks the VLA-4-mediated invasion by the cells. The inventors also find that vascular endothelial cells, which normally express VLA-4 and VEGFR2, also depend on this mechanism to respond to VLA-4 ligands during angiogenesis. These and other aspects of the disclosure are discussed below.

I. SYNDECANS

A. The Syndecan Family

Cell surface adhesion receptors physically bind cells to their extracellular matrix (ECM) and couple such interactions to intracellular signaling mechanisms which influence gene expression, cell morphology, motility, growth, differentiation and survival (Roskelley et al., 1995; Miranti and Brugge, 2002). Many ECM ligands contain closely spaced proteoglycan- and integrin-binding domains, indicating that the molecular mechanisms by which cells recognize and interact with their extracellular milieu may involve the formation of signaling complexes containing both proteoglycans and integrins. Consequentially, these two types of receptors may act in concert to modulate cell adhesion and migration. While the role of integrins in cell adhesion and signaling is well established, the role of heparan sulfate proteoglycans (HSPGs) is not well characterized.

The vertebrate syndecans are a family of four transmembrane HSPGs. Endowed by their heparan sulfate (HS) chains, syndecans bind a variety of ECM ligands, including fibronectin (FN), laminin (LN), tenascin, thrombospondin (TSP), vitronectin (VN) and the fibrillar collagens (COL) (Bernfield et al., 1999). While the syndecan HS chains are essential for matrix binding, less is known about the role of syndecan core proteins in cell adhesion signaling, although the core protein can affect ligand binding interactions, as well as occupancy induced signaling (Rapraeger and Ott, 1998; Rapraeger, 2000).

The syndecans display a high degree of conservation within their core proteins both across species and across family members. Like the integrins, the syndecans lack intrinsic signaling activity. Their short cytoplasmic tails (ca. 30 a.a.) consist of three regions, two of which are conserved amongst the four syndecans (C1 and C2) and which flank an intervening variable (V) region. Proteins known to interact with these conserved domains are believed to link syndecan ligand binding interactions to the transduction of intracellular signals (Couchman et al., 2001). Each family member is uniquely defined by its ectodomains and the V-regions of its cytoplasmic tail. Divergence within these regions is believed to confer separate and distinct functions to each individual family member. Distinct roles for the V-regions of Sdc-2 and -4 in matrix assembly and focal adhesion formation respectively have been described (Klass et al., 2000; Woods and Couchman, 2001); however, specific functions for the syndecan ectodomains are almost wholly unknown with the noted exception of the inventors' work on Sdc-1, which contains binding site for αvβ3 integrin/IGF-1R or α6β4 integrin/HER2 and Sdc-4 in which the inventors describe a binding site for as yet unidentified cell surface receptor(s) (McFall and Rapraeger, 1997; McFall and Rapraeger, 1998) and α6β4 integrin/EGFR (Wang et al., unpublished).

B. Syndecan Function in Cell Adhesion and Spreading

Current evidence suggests that the syndecan core proteins participate in adhesion-mediated signaling in collaboration with co-receptors at the cell surface. One example is Sdc-4 in focal adhesion and stress fiber formation, which requires both Sdc-4 and integrin engagement whereas neither is sufficient alone (Woods et al., 1986; Izzard et al., 1986; Streeter and Rees, 1987; Singer et al., 1987). The requirement for Sdc-4 ligation can be overcome by treatment with phorbol esters (Woods and Couchman, 1994) or lysophosphatidic acid (LPA) (Saoncella et al., 1999) implicating PKC and RhoA in Sdc-4 signaling. While the mechanism by which Sdc-4 contributes to RhoA activation is not clear, it is known that Sdc-4 interacts directly with PKCa as well as phosphatidyl inositol 4,5 bisphosphate (PIP2) via its cytoplasmic tail and these interactions potentiate PKCa activity (Oh et al., 1997a; Oh et al., 1997b; Oh et al., 1998; Baciu and Goetinck, 1995).

While the mechanism by which Sdc-1 signals is not clear, there is ample evidence implicating a signaling role for this receptor as well. Ectopic expression of Sdc-1 in Schwann cells enhances cell spreading and promotes the formation of focal adhesions (Hansen et al., 1994) and actin stress fibers (Carey et al., 1994a); similar morphological changes occur when Sdc-1 is co-clustered with antibodies (Carey et al., 1994b). This response requires the cytoplasmic domain, since clustering of a truncated core protein did not induce reorganization of the cytoskeleton. Expression of Sdc-1 in human ARH-77 leukemia cells or hepatocellular carcinoma cells inhibits invasion of cells into COL matrices (Liu et al., 1998; Ohtake et al., 1999). ARH-77 cells expressing a chimera comprised of the Sdc-1 ectodomain fused to the glycosyl-phosphatidyl inositol (GPI) tail of glypican-1 also fail to invade a COL matrix demonstrating that Sdc-1's anti-invasive activity resides in its extracellular domain. In similar studies, Raji human lymphoblastoid cells transfected with mouse Sdc-1 (Raji-S1) spread on TSP, FN and antibodies directed against the Sdc-1 ectodomain (Lebakken and Rapraeger, 1996). This spreading is unaffected by truncation of the cytoplasmic domain, indicating that the Sdc-1 core protein interacts with and cooperatively signals through an associated transmembrane signaling partner. Analogous features have also been observed for Sdc-2 (Granes et al., 1999) and Sdc-4 (Yamashita et al., 1999).

Potential syndecan signaling partners include cell surface integrins. Iba et al. (2000) demonstrated that mesenchymal cells when seeded on an HS-specific ligand, the cysteine rich domain of a disintegrin and metalloprotease, ADAM-12/Meltrin α (rADAM12-cys), will spread in a manner that requires cooperate signaling of both syndecans and $\beta_1$ integrins. These results imply that syndecan(s) can trigger signaling cascades required for cell spreading either by exposing a cryptic binding site for $\beta_1$ integrins, as has been proposed for FN (Khan et al., 1988), or by modulating the activation state of $\beta_1$ integrins. Interestingly, colon carcinoma cells attach but fail to spread on aADAM12-cys. However, exogenous stimulation of $\beta_1$ integrins with $Mn^{2+}$ or $\beta_1$ integrin function activating antibody, mAb 12G10, induced cell spreading, suggesting a mechanism whereby the syndecan activates $\beta_1$ integrins is blocked in transformed cells.

C. Syndecan-1

Syndecan-1 is highly expressed at the basolateral surface of epithelial cells where it is thought to interact with the actin cytoskeleton and to modulate cell adhesion and growth factor signaling (Bernfield et al., 1999; Rapraeger et al., 1986; Kim et al., 1994; Sanderson and Bernfield, 1988). In experimental studies of malignant transformation, Sdc-1 expression is associated with the maintenance of epithelial morphology, anchorage-dependent growth and inhibition of invasiveness. Alterations in syndecan expression during development (Sun et al., 1998) and in transformed epithelial (Inki and Jalkanen, 1996; Bayer-Garner et al., 2001) are associated with an epithelial-mesenchymal transformation with attendant alterations in cell morphology, motility, growth and differentiation. Transfection of epithelial cells with anti-sense mRNA for Sdc-1 or downregulation of Sdc-1 expression by androgen-induced transformation results in an epithelial to mesenchymal transformation and increased invasion (Leppa et al., 1992; Kato et al., 1995; Leppa et al., 1991). The loss of E-cadherin under these circumstances has long suggested a coordinate regulation of Sdc-1 and E-cadherin expression (Sun et al., 1998; Leppa et al., 1996). These studies, as well as others, indicate that there appears to be a threshold requirement for syndecan expression to elicit its biological activity. Syndecan-1 is downregulated in a number of epithelial cancers and in pre-malignant lesions of the oral mucosa (Soukka et al., 2000) and uterine cervix (Inki et al., 1994; Rintala et al., 1999; Nakanishi et al., 1999), and its loss may be an early genetic event contributing to tumor progression (Sanderson, 2001; Numa et al., 2002; Hirabayashi et al., 1998). Loss of Sdc-1 correlates with a reduced survival in squamous cell carcinoma of the head, neck and lung (Anttonen et al., 1999; Inki et al., 1994; Nakaerts et al., 1997), laryngeal cancer (Pulkkinen et al., 1997; Klatka, 2002), malignant mesothelioma (Kumar-Singh et al., 1998) and multiple myeloma (Sanderson and Borset, 2002) and a high metastatic potential in hepatocellular and colorectal carcinomas (Matsumoto et al., 1997; Fujiya et al., 2001; Levy et al., 1997; Levy et al., 1996). Downregulation of Sdc-2 and -4 expression has also been observed in certain human carcinomas (Nakaerts et al., 1997; Park et al., 2002; Mundhenke et al., 2002; Crescimanno et al., 1999), but the functional consequences of these alterations in expression are less clear.

In contrast to the general notion that the syndecan may be an inhibitor of carcinogenesis, Sdc-1 also demonstrates tumor promoter function. Syndecan-1 supplements Wnt-1 induced tumorigenesis of the mouse mammary gland (Alexander et al., 2000) and promotes the formation of metastases in mouse lung squamous carcinoma cells (Hirabayashi et al., 1998). Enhanced Sdc-1 expression has also been observed in pancreatic (Conejo et al., 2000), gastric (Wiksten et al., 2001) and breast (Burbach et al., 2003; Stanley et al., 1999; Barbareschi et al., 2003) carcinomas and this overexpression correlates with increased tumor aggressiveness and poor clinical prognosis. This duality in the role of Sdc-1 in tumorigenesis may reflect tissue and/or tumor stage-specific function, or reflect the multiple functions of this PG.

Sanderson was the first to demonstrate a role for Sdc-1 in tumor cell migration by examining the invasion of myeloma cells into collagen gels (Liu et al., 1998). Ectopic expression of Sdc-1 in syndecan-deficient myeloma cells had the striking effect of curtailing invasion, whereas the expression of other cell surface heparan sulfate PGs (e.g., glypican) was without effect. Using chimeras derived from these two proteins, Sanderson showed that the activity of the syndecan is preserved when its ectodomain alone is expressed as a glycosyl-phosphatidylinositol (GPI)-linked protein at the cell surface. Although clearly responsible for binding the collagen matrix via its attached heparan sulfate chains, the anti-invasive activity of the syndecan requires yet an additional interaction that traces to a site in the extracellular domain of the core protein itself. The mechanism by which the ectodomain site influences the invasion of the myeloma cells is unknown, but its interaction with other cell surface receptors in a "co-receptor" role is one possibility. More recently, ectopic expression of Sdc-1 has also been shown to curtail the invasion of hepatocellular carcinoma cells into a collagen matrix (Ohtake et al., 1999).

II. INTEGRINS AND VEGFR2

A. VLA-4 (α4β1 Integrin)

Integrins are receptors that mediate attachment between a cell and the tissues surrounding it, which may be other cells or the ECM. They also play a role in cell signaling and thereby regulate cellular shape, motility, and the cell cycle.

Typically, receptors inform a cell of the molecules in its environment and the cell responds. Not only do integrins perform this outside-in signalling, but they also operate an inside-out mode. Thus, they transduce information from the ECM to the cell as well as reveal the status of the cell to the outside, allowing rapid and flexible responses to changes in the environment, for example to allow blood coagulation by platelets.

There are many types of integrin, and many cells have multiple types on their surface. Integrins are of vital importance to all animals and have been found in all animals investigated, from sponges to mammals. Integrins have been extensively studied in humans.

Integrins work alongside other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

Integrin α4β1 (Very Late Antigen-4) is an integrin dimer. It is composed of CD49d (α4) and CD29 (β1). Vascular cell adhesion molecule-1 (VCAM-1—an integrin receptor) located on an endothelial cell, binds to VLA-4 which are normally expressed on leukocyte plasma membranes, but they do not adhere to their appropriate ligands until the leukocytes are activated by chemotactic agents or other stimuli (often produced by the endothelium or other cells at the site of injury). Only then do the integrins undergo the conformational change necessary to confer high binding affinity for the endothelial adhesion molecules.

In multiple sclerosis, the VLA-4 integrin is essential in the processes by which T-cells gain access to the brain by allowing the cells to penetrate the blood brain barrier that normally restricts immune cell access. One approach to prevent an autoimmune reaction has been to block the action of VLA-4 so that self-reactive T-cells are unable to enter the brain and thus unable to attack myelin protein.

Vascular endothelial and lymphatic endothelial cells also depend on VLA-4. VLA4 expression is required for angiogenesis by both vascular and lymphatic endothelial cells and its activity is especially prominent in tumors. Its matrix ligand, FN, is deposited within the growing vascular and lymphatic microvessels and VCAM-1 is prominently expressed on mural cells (pericytes) that support vascular endothelial cells.[13-15] In recent years antagonists of VLA-4 have shown great promise in treating inflammatory disorders in a number of animal models. However, the usage of Natalizumab, an antagonist of VLA-4 integrin, remains controversial due to several side effects including Progressive multifocal leukoencephalopathy.

B. VEGFR2

VEGF receptors are receptors for vascular endothelial growth factor (VEGF). There are three main subtypes of VEGFR, numbered 1, 2 and 3. Also, they may be membrane-bound (mbVEGFR) or soluble (sVEGFR), depending on alternative splicing.

Vascular endothelial growth factor (VEGF) is an important signaling protein involved in both vasculogenesis (the formation of the circulatory system) and angiogenesis (the growth of blood vessels from pre-existing vasculature). As its name implies, VEGF activity is restricted mainly to cells of the vascular endothelium, although it does have effects on a limited number of other cell types (e.g., stimulation monocyte/macrophage migration). In vitro, VEGF has been shown to stimulate endothelial cell mitogenesis and cell migration. VEGF also enhances microvascular permeability and is sometimes referred to as vascular permeability factor.

All members of the VEGF family stimulate cellular responses by binding to tyrosine kinase receptors (the VEGFRs) on the cell surface, causing them to dimerize and become activated through transphosphorylation. The VEGF receptors have an extracellular portion consisting of 7 immunoglobulin-like domains, a single transmembrane spanning region and an intracellular portion containing a split tyrosine-kinase domain.

VEGF-A binds to VEGFR1 (Flt-1) and VEGFR2 (Kinase insert domain receptor; KDR/Flk-1). VEGFR2 appears to mediate almost all of the known cellular responses to VEGF. The function of VEGFR1 is less well defined, although it is thought to modulate VEGFR2 signaling. Another function of VEGFR-1 is to act as a dummy/decoy receptor, sequestering VEGF from VEGFR2 binding (this appears to be particularly important during vasculogenesis in the embryo). In fact, an alternatively spliced form of VEGFR1 (sFlt1) is not a membrane bound protein but is secreted and functions primarily as a decoy. A third receptor has been discovered (VEGFR3), however, VEGF-A is not a ligand for this receptor. VEGFR3 mediates lymphangiogenesis in response to VEGF-C and VEGF-D.

KDR (VEGFR2), a type III receptor tyrosine kinase, has also been designated as CD309 (cluster of differentiation 309). KDR is also known as Flk1 (Fetal Liver Kinase 1). KDR has been shown to interact with SHC2, Annexin A5 and SHC1.

III. SYNDECAN PEPTIDES

A. Structure

The present disclosure contemplates the design, production and use of various syndecan peptides. The structural features of these peptides are as follows. First, the peptides have about 23 consecutive residues of a syndecan and up to 100 consecutive residues. Thus, the term "a peptide having no more than X consecutive residues," even when including the term "comprising," cannot be understood to comprise a greater number of consecutive syndecan residues. Second, the peptides will contain the motifs responsible for interaction with VEGFR2 or VLA-4. In general, the peptides will have, at a minimum, 25 or more consecutive residues of the syndecan.

In general, the peptides will be 100 residues or less, again, comprising no more than 23-100 consecutive residues of a syndecan. The overall length may be 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 residues. Ranges of peptide length of 23-50 residues, 23-27 residues, 23-30, residues, 23-40 residues, 23-60, residues, 23-70 residues, 23-80 residues, 23-90 residues, and 23-100 residues are contemplated. The number of consecutive syndecan residues may be 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 residues, including 23-50 residues, 23-27 residues, 23-30, residues, 23-40 residues, 23-60, residues, 23-70 residues, 23-80 residues, 23-90 residues, and 23-100.

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse syndecan peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al. (2000).

D. Design, Variants and Analogs

Having identified structures in VEFGR2 interaction with VLA-4 integrins, the inventor also contemplates that variants of the sequences may be employed. For example, certain non-natural amino acids that satisfy the structural constraints of the sequences may be substituted without a loss, and perhaps with an improvement in, biological function. In addition, the present inventor also contemplates that structurally similar compounds may be formulated to mimic the key portions of peptide or polypeptides of the present disclosure. Such compounds, which may be termed peptidomimetics, may be used in the same manner as the peptides of the disclosure and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the disclosure also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., PCT/US99/11913, incorporated herein by reference in its entirety). Other molecular modeling techniques may also be employed in accordance with this disclosure (e.g., Cohen et al., 1990; Navia et al., 1992), the disclosures of which are incorporated herein by reference in their entirety). All these methods produce data that are amenable to computer analysis. Other spectroscopic methods that can also be useful in the method of the disclosure, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

The present disclosure may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

X-Ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between $-220°$ C. and $-50°$ C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573, PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the disclosure that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the interaction of VLA-4 and VEGR2. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous media. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, purity and general safety standards as required by FDA Office of Biologics Standards.

B. Treatment Methods Involving Inhibition

It is envisioned that a peptide that contains binding sites for both VEGFR2 and VLA-4, such as 210-236, has the capacity to bridge both receptors and link them together. This activates signaling that the cells use for migration and invasion. The inventors work (FIGS. 6A-H) demonstrates that 210-236 displays such activity with an $EC_{50}$ of 0.3 µM. At 30-100-fold higher concentrations, e.g., 10-30 µM, same peptide would compete with itself such that it would occupy only single receptors using one or the other binding motif; it would not couple the receptors together even though it contained both binding sites, and would prevent endogenous Sdc1 from the binding sites and coupling the receptors, thus acting as effective inhibitors of the mechanism. The inventors have shown that 210-236 acts as such an inhibitor with an $IC_{50}$ of 10 µM. Administration of peptide such that serum levels of peptide reach either the $EC_{50}$ or $IC_{50}$ concentration would be used to manipulate the activating or inhibitory activity.

1. Cancer

Cancer cells to which the methods of the present disclosure can be applied include generally any cell that expresses VEGFR2 and/or VLA-4, and more particularly, that over-expresses VEGFR2 and/or VLA-4. An appropriate cancer cell can be a breast cancer, lung cancer, colon cancer, pancreatic cancer, renal cancer, stomach cancer, liver cancer, bone cancer, hematological cancer (e.g., leukemia or lymphoma), myeloma (including multiple myeloma), neural tissue cancer, melanoma, ovarian cancer, testicular cancer, prostate cancer, cervical cancer, vaginal cancer, or bladder cancer cell. In addition, the methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

Peptides or analogs that inhibit Sdc1 engagement to VLA-4, or VLA-4 engagement of VEGFR2 can be administered to mammalian subjects (e.g., human breast cancer patients) alone or in conjunction with other drugs and/or radiotherapy. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

When the methods are applied to subjects with cancer, prior to administration of a compound, the cancer can optionally be tested for VEGFR2 and/or VLA-4 expression or overexpression by methods known in the art. In this way, subjects can be identified as being susceptible to treatments according to the present disclosure. Such methods can be performed in vitro on cancer cells obtained from a subject. Alternatively, in vivo imaging techniques using, for example, radiolabeled antibodies specific for VEGFR2 and/or VLA-4 can be performed.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

2. Pathologic Wound Healing

Wound healing is an essential process in maintaining health. However, in certain instances, wound healing can create health problems. These include hypertrophic scarring, keloid or dermoid formation, and exuberant granulation. These conditions are often supported by pathologic angiogenesis (discussed below). The present disclosure may be applied to address these conditions.

i. Keloids

A keloid is a type of scar that, depending on its maturity, is composed mainly of either type III (early) or type I (late) collagen. It is a result of an overgrowth of granulation tissue (collagen type 3) at the site of a healed skin injury which is then slowly replaced by collagen type 1. Keloids are firm, rubbery lesions or shiny, fibrous nodules, and can vary from pink to flesh-coloured or red to dark brown in colour. A keloid scar is benign, non-contagious, but sometimes accompanied by severe itchiness and pain, and changes in texture. In severe cases, it can affect movement of skin.

Keloids should not be confused with hypertrophic scars, which are raised scars that do not grow beyond the boundaries of the original wound. Keloids expand in claw-like growths over normal skin. They have the capability to hurt with a needle-like pain or to itch without warning, although the degree of sensation varies from patient to patient.

If the keloid becomes infected, it may ulcerate. Removing the scar is one treatment option; however, it may result in more severe consequences: the probability that the resulting surgery scar will also become a keloid is high, usually greater than 50%. Laser treatment has also been used with varying degrees of success.

Keloids form within scar tissue. Collagen, used in wound repair, tends to overgrow in this area, sometimes producing a lump many times larger than that of the original scar. Although they usually occur at the site of an injury, keloids can also arise spontaneously. They can occur at the site of a piercing and even from something as simple as a pimple or scratch. They can occur as a result of severe acne or chickenpox scarring, infection at a wound site, repeated trauma to an area, excessive skin tension during wound closure or a foreign body in a wound. Keloids can sometimes be sensitive to chlorine. Keloid scars can grow, if they appear at a younger age, because the body is still growing.

Histologically, keloids are fibrotic tumors characterized by a collection of atypical fibroblasts with excessive deposition of extracellular matrix components, especially collagen, fibronectin, elastin, and proteoglycans. Generally, keloids contain relatively acellular centers and thick, abundant collagen bundles that form nodules in the deep dermal portion of the lesion. Keloids present a therapeutic challenge that must be addressed, as these lesions can cause significant pain, pruritus (itching), and physical disfigurement. They may not improve in appearance over time and can limit mobility if located over a joint.

Keloids affect both sexes equally, although the incidence in young female patients has been reported to be higher than in young males, probably reflecting the greater frequency of earlobe piercing among women. There is a fifteen times higher frequency of occurrence in highly pigmented people. Persons of African descent are at increased risk of keloid occurrences.

The best treatment is prevention in patients with a known predisposition. This includes preventing unnecessary trauma or surgery (including ear piercing, elective mole removal), whenever possible. Any skin problems in predisposed individuals (e.g., acne, infections) should be treated as early as possible to minimize areas of inflammation.

Intra-Lesional Corticosteroids.

Intra-lesional corticosteroids are first-line therapy for most keloids. A systematic review found that up to 70 percent of patients respond to intra-lesional corticosteroid injection with flattening of keloids, although the recurrence rate is high in some studies (up to 50 percent at five years). While corticosteroids are one of the more common treatments, injections into and in close proximity to keloid tissue can be highly painful and can produce undesirable results in female patients, as per any other testosterone-based treatment.

Excision.

Scalpel excision may be indicated if injection therapy alone is unsuccessful or unlikely to result in significant improvement. Excision should be combined with preoperative, intraoperative, or postoperative triamcinolone or interferon injections. Recurrence rates from 45 to 100 percent have been reported in patients treated with excision alone; this falls to below 50 percent in patients treated with combination therapy.

Gel Sheeting.

Both hydrogel and silicone gel sheeting have been used for the treatment of symptoms (e.g., pain and itching) in patients with established keloids as well as for the management of evolving keloids and the prevention of keloids at the sites of new injuries. While the precise mechanism of action is still poorly understood, there is evidence that application of gel sheeting may reduce the incidence of abnormal scarring. A controlled study found significant changes in growth factor levels of fibronectin and IL-8 with application of hydrogel sheeting with respect to normal skin. Silicone sheeting was associated with changing growth factor levels of only fibronectin.

Cryosurgery.

Cryosurgery is most useful in combination with other treatments for keloids. The major side effect is permanent hypopigmentation, which limits its use in people with darker skin.

Radiation Therapy.

Most studies, but not all, have found radiation therapy to be highly effective in reducing keloid recurrence, with improvement rates of 70 to 90 percent when administered after surgical excision. A small randomized trial of treatments after surgery found recurrences in two of sixteen earlobe keloids (13 percent) treated with radiation therapy and in four of twelve earlobe keloids (33 percent) treated with steroid injections. However, concern regarding the potential long-term risks (e.g., malignancy) associated with using radiation for an essentially benign disorder limits its utility in most patients. Only a few cases of malignancy that may have been associated with radiation therapy for keloids have been reported. Although causation cannot be confirmed in these cases, caution should still be used when prescribing radiation therapy for keloids, particularly when treating younger patients. Radiation therapy may occasionally be appropriate as treatment for keloids that are resistant to other therapies. In addition, radiation therapy may be indicated for lesions that are not amenable to resection.

Interferon Alpha.

Interferon alpha injections may reduce recurrence rates postoperatively. However, all currently available studies of interferon therapy suffer from methodologic problems, making an evidence-based recommendation regarding its use difficult.

Pulsed Dye Laser.

Pulsed dye laser treatment can be beneficial for keloids, and appears to induce keloid regression through suppression of keloid fibroblast proliferation, and induction of apoptosis and enzyme activity. Combination treatment with pulsed dye laser plus intralesional therapy with corticosteroids and/or fluorouracil may be superior to either approach alone.

ii. Hypertrophic Scarring

Hypertrophic scars are a cutaneous condition characterized by deposits of excessive amounts of collagen which gives rise to a raised scar, but not to the degree observed with keloids. Like keloids, they form most often at the sites of pimples, body piercings, cuts and burns. They often contain nerves and blood vessels. They generally develop after thermal or traumatic injury that involves the deep layers of the dermis and express high levels of TGF-β.

When a normal wound heals the body produces new collagen fibers at a rate which balances the breakdown of old collagen. Hypertrophic scars are red and thick and may be itchy or painful. They do not extend beyond the boundary of the original wound but may continue to thicken for up to 6 months. They usually improve over the one or two years but may cause distress due to their appearance or the intensity of the itching, also restricting movement if they are located close to a joint.

Hypertrophic scars are more common in the young and people with darker skin. Some people have an inherited tendency to this type of scarring. It is not possible to completely prevent hypertrophic scars, so anyone who has suffered one should inform their doctor or surgeon if they need to have surgery. Scar therapies are available which may speed up the process of change from a hypertrophic scar to a flatter, paler one. Scars do not occur in younger people as often as older people because their skin cells replicate more quickly and fill in the wound with normal skin tissue.

iii. Proud Flesh

Granulation tissue is the perfused, fibrous connective tissue that replaces a fibrin clot in healing wounds. Granulation tissue typically grows from the base of a wound and is able to fill wounds of almost any size it heals. In addition, it is also found in ulcers like esophageal ulcer; however, when the granulation becomes uncontrolled, often resulting from improper wound care, a condition known as exuberant granulation or "proud flesh" results. The scar tissue, if untreated, may completely overtake the wound area. Caught early, the condition can be treated by topical or injected steroids, but more advanced cases require surgical intervention. Horses are subject to this disease, particularly in the legs. Also, some individuals of African decent have a genetic predisposition to exuberant scarring.

3. Pathologic Angiogenesis

Despite the abundancy of angiogenic factors present in different tissues, endothelial cell turnover in a healthy adult organism is remarkably low with a turnover in the order of thousands of days. The maintenance of endothelial quiescence is thought to be due to the presence of endogenous negative regulators. Moreover, positive and negative regulators often co-exist in tissues with extensive angiogenesis. These observations have led to the hypothesis that activation of the endothelium depends on a balance between these opposing regulators. If positive angiogenic factors dominate, the endothelium will be activated. Thus, the angiogenic process can be divided in an activation phase (initiation and progression of the angiogenic process) and a phase of resolution (termination and stabilization of the vessels). It is not yet clear whether the resolution phase is due to upregulation of endogenous inhibitors or exhaustion of positive regulators.

With respect to activated endothelium, an important distinction must be made between physiological and pathological settings. Although many positive and negative regulators operate in both, endothelial cell proliferation is tightly controlled in the former, whereas in the latter, the uncontrolled growth of microvessels may lead to several "angiogenic diseases" in different tissues, such as hemangiomas, psoriasis, Kaposi's sarcoma, ocular neovascularization, rheumatoid arthritis, endometriosis, atherosclerosis, tumor growth and metastasis, myocardial ischemia, peripheral ischemia, cerebral ischemia, wound healing, reconstructive surgery, and ulcer healing, and these may also be advantageously treated with the compositions of the present disclosure. Some of these are discussed in greater detail below.

Hemangiomas are angiogenic diseases, characterized by the proliferation of capillary endothelium with accumulation of mast cells, fibroblasts and macrophages. They represent the most frequent tumors of infancy, occurring more frequently in females than males (3:1 ratio). Hemangiomas are characterized by rapid neonatal growth (proliferating phase). By the age of 6 to 10 months, the hemangioma's growth rate becomes proportional to the growth rate of the child, followed by a very slow regression for the next 5 to 8 years (involuting phase). Most hemangiomas occur as single tumors whereas about 20% of the affected infants have multiple tumors, which may appear at any body site. Approximately 5% produce life-, sight-, or limb-threatening complications, with high mortality rates. The pathogenesis of hemangiomas has not yet been elucidated. However, several immunohistochemical studies have provided insight into the histopathology of these lesions. In particular, proliferating hemangiomas express high levels of proliferating cell nuclear antigen (PCNA, a marker for cells in the S phase), type IV collagenase, VEGF and FGF-2. During the involuting phase of hemangiomas, expression of these angiogenic factors decreases. Furthermore, urinary levels of FGF-2 are elevated during the proliferating phase of hemangioma, but become normal during involution or after therapy with IFN-α.

Other proliferative disorders of the skin include psoriasis and Kaposi's sarcoma. Hypervascular psoriatic lesions express high levels of the angiogenic inducer IL-8, whereas the expression of the endogenous inhibitor TSP-1 is decreased. Kaposi's sarcoma (KS) is the most common tumor associated with human immunodeficiency virus (HIV) infection and is in this setting almost always associated with human herpes virus 8 (HHV-8) infection. Typical features of KS are proliferating spindle-shaped cells, considered to be the tumor cells and endothelial cells forming blood vessels. KS is a cytokine-mediated disease, highly responsive to different inflammatory mediators like IL-10, TNF-α and IFN-γ and angiogenic factors. In particular, FGF-2 was found to synergize with HIV-tat to promote angiogenesis and KS development. Finally, growth of KS, both in vitro and in vivo, could be blocked by an antisense oligonucleotide targeting FGF-2.

Diabetic retinopathy is the leading cause of blindness in the working population, but ocular neovascularization can also occur upon exposure of preterm babies to oxygen. It is assumed that both forms are induced by hypoxia in the retina. Elevated levels of the hypoxia-inducible angiogenic factor VEGF were detected in the aqueous and vitreous of eyes with proliferative retinopathy.

Excessive production of angiogenic factors from infiltrating macrophages, immune cells or inflammatory cells may also trigger the formation of pannus, an extensively vascularized tissue that invades and destroys the cartilage, as seen in rheumatoid arthritis. Moreover, uncontrolled angiogenesis may underlie various female reproductive disorders, such as prolonged menstrual bleeding or infertility, and excessive endothelial cell proliferation has been observed in the endometrium of women with endometriosis.

Angiogenesis also contributes to atherosclerosis, a major cause of death of Western populations. Atherosclerosis is the main cause of heart attack. The walls of the coronary artery are normally free of microvessels except in the atherosclerotic plaques, where there are dense networks of capillaries, known as the vasa vasorum. These fragile microvessels can cause hemorrhages, leading to blood clotting, with a subsequent decreased blood flow to the heart muscle and heart attack. Finally, angiogenesis is thought to be indispensable for solid tumor growth and metastasis.

4. Inflammatory and Autoimmune Diseases

In another aspect, the inventors contemplate the treatment of various inflammatory and autoimmune diseases with the peptide agents described herein. Non-limiting examples of such diseases are set forth below.

i. Inflammatory Bowel Disease

Ulcerative Colitis.

Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions—periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

The goal of therapy is to induce and maintain remission, and to improve the quality of life for people with ulcerative colitis. Several types of drugs are available. Aminosalicylates are drugs that contain 5-aminosalicyclic acid (5-ASA), help control inflammation. Sulfasalazine is a combination of sulfapyridine and 5-ASA and is used to induce and maintain remission. The sulfapyridine component carries the anti-inflammatory 5-ASA to the intestine. However, sulfapyridine may lead to side effects such as include nausea, vomiting, heartburn, diarrhea, and headache. Other 5-ASA agents such as olsalazine, mesalamine, and balsalazide, have a different carrier, offer fewer side effects, and may be used by people who cannot take sulfasalazine. 5-ASAs are given orally, through an enema, or in a suppository, depending on the location of the inflammation in the colon. Most people with mild or moderate ulcerative colitis are treated with this group of drugs first. Corticosteroids such as prednisone and hydrocortisone also reduce inflammation. They may be used by people who have moderate to severe ulcerative colitis or who do not respond to 5-ASA drugs. Corticosteroids, also known as steroids, can be given orally, intravenously, through an enema, or in a suppository, depending on the location of the inflammation. These drugs can cause side effects such as weight gain, acne, facial hair, hypertension, mood swings, and an increased risk of infection. For this reason, they are not recommended for long-term use. Immunomodulators such as azathioprine and 6-mercapto-purine (6-MP) reduce inflammation by affecting the immune system. They are used for patients who have not responded to 5-ASAs or corticosteroids or who are dependent on corticosteroids. However, immunomodulators are slow-acting and may take up to 6 months before the full benefit is seen. Patients taking these drugs are monitored for complications including pancreatitis and hepatitis, a reduced white blood cell count, and an increased risk of infection. Cyclosporine A may be used with 6-MP or azathioprine to treat active, severe ulcerative colitis in people who do not respond to intravenous corticosteroids. Other drugs may be given to relax the patient or to relieve pain, diarrhea, or infection.

Occasionally, symptoms are severe enough that the person must be hospitalized. For example, a person may have severe bleeding or severe diarrhea that causes dehydration. In such cases the doctor will try to stop diarrhea and loss of blood, fluids, and mineral salts. The patient may need a special diet, feeding through a vein, medications, or sometimes surgery.

About 25-40% of ulcerative colitis patients must eventually have their colons removed because of massive bleeding, severe illness, rupture of the colon, or risk of cancer. Sometimes the doctor will recommend removing the colon if medical treatment fails or if the side effects of corticosteroids or other drugs threaten the patient's health. Surgery to remove the colon and rectum, known as proctocolectomy, is followed by one of the following:

Ileostomy, in which the surgeon creates a small opening in the abdomen, called a stoma, and attaches the end of the small intestine, called the ileum, to it. Waste will travel through the small intestine and exit the body through the stoma. The stoma is about the size of a quarter and is usually located in the lower right part of the abdomen near the beltline. A pouch is worn over the opening to collect waste, and the patient empties the pouch as needed.

Ileoanal anastomosis, or pull-through operation, which allows the patient to have normal bowel movements because it preserves part of the anus. In this operation, the surgeon removes the diseased part of the colon and the inside of the rectum, leaving the outer muscles of the rectum. The surgeon then attaches the ileum to the inside of the rectum and the anus, creating a pouch. Waste is stored in the pouch and passed through the anus in the usual manner. Bowel movements may be more frequent and watery than before the procedure. Inflammation of the pouch (pouchitis) is a possible complication.

Not every operation is appropriate for every person. Which surgery to have depends on the severity of the disease and the patient's needs, expectations, and lifestyle. People faced with this decision should get as much information as possible by talking to their doctors, to nurses who work with colon surgery patients (enterostomal therapists), and to other colon surgery patients. Patient advocacy organizations can direct people to support groups and other information resources.

Most people with ulcerative colitis will never need to have surgery. If surgery does become necessary, however, some people find comfort in knowing that after the surgery, the colitis is cured and most people go on to live normal, active lives.

Crohn's Disease.

Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective. Immunosuppression with cyclosporine is sometimes beneficial for patients resistant to or intolerant of corticosteroids. Nevertheless, surgical correction is eventually required in 90% of patients; 50% undergo colonic resection. The recurrence rate after surgery is high, with 50% requiring further surgery within 5 years.

One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens. Another hypothesis is that persistent intestinal infection by pathogens such as *Mycobacterium paratuberculosis, Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce. The presence of IgA and IgG anti-*Sacccharomyces cerevisiae* antibodies (ASCA) in the serum was found to be highly diagnostic of pediatric Crohn's disease.

In Crohn's disease, a dysregulated immune response is skewed toward cell-mediated immunopathology. But immunosuppressive drugs, such as cyclosporine, tacrolimus, and mesalamine have been used to treat corticosteroid-resistant cases of Crohn's disease with mixed success.

Treatments that have been proposed for Crohn's disease include the use of various cytokine antagonists (e.g., IL-1ra), inhibitors (e.g., of IL-1β converting enzyme and antioxidants) and anti-cytokine antibodies. In particular, monoclonal antibodies against TNF-α have been tried with some success in the treatment of Crohn's disease. Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. However, there has been no known cause of Crohn's disease to which diagnosis and/or treatment could be directed.

Rheumatoid Arthritis.

The exact etiology of RA remains unknown, but the first signs of joint disease appear in the synovial lining layer, with proliferation of synovial fibroblasts and their attachment to the articular surface at the joint margin. Subsequently, macrophages, T cells and other inflammatory cells are recruited into the joint, where they produce a number of mediators, including the cytokines interleukin-1 (IL-1), which contributes to the chronic sequalae leading to bone and cartilage destruction, and tumour necrosis factor (TNF-α), which plays a role in inflammation. The concentration of IL-1 in plasma is significantly higher in patients with RA than in healthy individuals and, notably, plasma IL-1 levels correlate with RA disease activity. Moreover, synovial fluid levels of IL-1 are correlated with various radiographic and histologic features of RA.

In normal joints, the effects of these and other proinflammatory cytokines are balanced by a variety of anti-inflammatory cytokines and regulatory factors. The significance of this cytokine balance is illustrated in juvenile RA patients, who have cyclical increases in fever throughout the day. After each peak in fever, a factor that blocks the effects of IL-1 is found in serum and urine. This factor has been isolated, cloned and identified as IL-1 receptor antagonist (IL-1ra), a member of the IL-1 gene family. IL-1ra, as its name indicates, is a natural receptor antagonist that competes with IL-1 for binding to type I IL-1 receptors and, as a result, blocks the effects of IL-1. A 10- to 100-fold excess of IL-1ra may be needed to block IL-1 effectively; however, synovial cells isolated from patients with RA do not appear to produce enough IL-1ra to counteract the effects of IL-1.

ii. Systemic Lupus Erythematosus

There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable. For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (GN). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

The mechanisms by which autoantibodies are induced in these autoimmune diseases remains unclear. As there has been no known cause of SLE, to which diagnosis and/or treatment could be directed, treatment has been directed to suppressing immune responses, for example with macrolide antibiotics, rather than to an underlying cause. (e.g., U.S. Pat. No. 4,843,092).

iii. Multiple Sclerosis

Multiple sclerosis (MS), also known as disseminated sclerosis or encephalomyelitis disseminata, is an inflammatory disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems. MS takes several forms, with new symptoms either occurring in isolated attacks (relapsing forms) or building up over time (progressive forms). Between attacks, symptoms may disappear completely; however, permanent neurological problems often occur, especially as the disease advances.

Multiple sclerosis is the most common autoimmune disorder affecting the central nervous system. As of 2008, between 2 and 2.5 million people are affected globally with rates varying widely in different regions of the world and among different populations. The disease usually begins between the ages of 20 and 50 and is twice as common in women as in men. The name multiple sclerosis refers to scars (sclerae-better known as plaques or lesions) in particular in the white matter of the brain and spinal cord.

A person with MS can have almost any neurological symptom or sign; with autonomic, visual, motor, and sensory problems being the most common. The specific symptoms are determined by the locations of the lesions within the nervous system, and may include loss of sensitivity or changes in sensation such as tingling, pins and needles or numbness, muscle weakness, very pronounced reflexes, muscle spasms, or difficulty in moving; difficulties with coordination and balance (ataxia); problems with speech or swallowing, visual problems (nystagmus, optic neuritis or double vision), feeling tired, acute or chronic pain, and bladder and bowel difficulties, among others. Difficulties thinking and emotional problems such as depression or unstable mood are also common. Uhthoffs phenomenon, a worsening of symptoms due to exposure to higher than usual temperatures, and Lhermitte's sign, an electrical sensation that runs down the back when bending the neck, are particularly characteristic of MS. The main measure of disability and severity is the expanded disability status scale (EDSS), with other measures such as the multiple sclerosis functional composite being increasingly used in research.

The condition begins in 85% of cases as a clinically isolated syndrome over a number of days with 45% having motor or sensory problems, 20% having optic neuritis, and 10% having symptoms related to brainstem dysfunction, while the remaining 25% have more than one of the previous difficulties. The course of symptoms occurs in two main patterns initially: either as episodes of sudden worsening that last a few days to months (called relapses, exacerbations, bouts, attacks, or flare-ups) followed by improvement (85% of cases) or as a gradual worsening over time without periods of recovery (10-15% of cases). A combination of these two patterns may also occur or people may start in a relapsing and remitting course that then becomes progressive later on. Relapses are usually not predictable, occurring without warning. Exacerbations rarely occur more frequently than twice per year. Some relapses, however, are preceded by common triggers and they occur more frequently during spring and summer. Similarly, viral infections such as the common cold, influenza, or gastroenteritis increase their risk. Stress may also trigger an attack. Women with MS who become pregnant experience fewer relapses; however, during the first months after delivery the risk increases. Overall, pregnancy does not seem to influence long-term disability. Many events have not been found to affect relapse rates including vaccination, breast feeding, physical trauma, and Uhthoffs phenomenon.

The cause of MS is unknown; however, it is believed to occur as a result of some combination of environmental factors such as infectious agents and genetics. Theories try to combine the data into likely explanations, but none has proved definitive. While there are a number of environmental risk factors and although some are partly modifiable, further research is needed to determine whether their elimination can prevent MS.

MS is more common in people who live farther from the equator, although exceptions exist. These exceptions include ethnic groups that are at low risk far from the equator such as the Samis, Amerindians, Canadian Hutterites, New Zealand Maori, and Canada's Inuit, as well as groups that have a relatively high risk close to the equator such as Sardinians, inland Sicilians, Palestinians and Parsis. The cause of this geographical pattern is not clear. While the north-south gradient of incidence is decreasing, as of 2010 it is still present.

MS is more common in regions with northern European populations and the geographic variation may simply reflect the global distribution of these high-risk populations. Decreased sunlight exposure resulting in decreased vitamin D production has also been put forward as an explanation. A relationship between season of birth and MS lends support to this idea, with fewer people born in the northern hemisphere in November as compared to May being affected later in life. Environmental factors may play a role during childhood, with several studies finding that people who move to a different region of the world before the age of 15 acquire the new region's risk to MS. If migration takes place after age 15, however, the person retains the risk of his home country. There is some evidence that the effect of moving may still apply to people older than 15.

MS is not considered a hereditary disease; however, a number of genetic variations have been shown to increase the risk. The probability is higher in relatives of an affected person, with a greater risk among those more closely related. In identical twins both are affected about 30% of the time, while around 5% for non-identical twins and 2.5% of siblings are affected with a lower percentage of half-siblings. If both parents are affected the risk in their children is 10 times that of the general population. MS is also more common in some ethnic groups than others.

Specific genes that have been linked with MS include differences in the human leukocyte antigen (HLA) system—a group of genes on chromosome 6 that serves as the major histocompatibility complex (MHC). That changes in the HLA region are related to susceptibility has been known for over thirty years, and additionally this same region has been implicated in the development of other autoimmune diseases such as diabetes type I and systemic lupus erythematosus. The most consistent finding is the association between multiple sclerosis and alleles of the MHC defined as DR15 and DQ6. Other loci have shown a protective effect, such as HLA-C554 and HLA-DRB 1*11. Overall, it has been estimated that HLA changes account for between 20 and 60% of the genetic predisposition. Modern genetic methods (genome-wide association studies) have discovered at least twelve other genes outside the HLA locus that modestly increase the probability of MS.

Many microbes have been proposed as triggers of MS, but none have been confirmed. Moving at an early age from one location in the world to another alters a person's subsequent risk of MS. An explanation for this could be that some kind of infection, produced by a widespread microbe rather than a rare one, is related to the disease. Proposed mechanisms include the hygiene hypothesis and the prevalence hypothesis. The hygiene hypothesis proposes that exposure to certain infectious agents early in life is protective, the disease being a response to a late encounter with such agents. The prevalence hypothesis proposes that the disease is due to an infectious agent more common in regions where MS is common and where in most individuals it causes an ongoing infection without symptoms. Only in a few cases and after many years does it cause demyelination. The hygiene hypothesis has received more support than the prevalence hypothesis.

Evidence for a virus as a cause include: the presence of oligoclonal bands in the brain and cerebrospinal fluid of most people with MS, the association of several viruses with human demyelination encephalomyelitis, and the occurrence of demyelination in animals caused by some viral infection. Human herpes viruses are a candidate group of viruses. Individuals having never been infected by the Epstein-Barr virus are at a reduced risk of getting MS, whereas those infected as young adults are at a greater risk than those having had it at a younger age. Although some consider that this goes against the hygiene hypothesis, since the non-infected have probably experienced a more hygienic upbringing, others believe that there is no contradiction, since it is a first encounter with the causative virus relatively late in life that is the trigger for the disease. Other diseases that may be related include measles, mumps and rubella.

Smoking has been shown to be an independent risk factor for MS. Stress may be a risk factor although the evidence to support this is weak. Association with occupational exposures and toxins—mainly solvents—has been evaluated, but no clear conclusions have been reached. Vaccinations were studied as causal factors; however, most studies show no association. Several other possible risk factors, such as diet and hormone intake, have been looked at; however, evidence on their relation with the disease is "sparse and unpersuasive". Gout occurs less than would be expected and lower levels of uric acid have been found in people with MS. This has led to the theory that uric acid is protective, although its exact importance remains unknown.

Multiple sclerosis is typically diagnosed based on the presenting signs and symptoms, in combination with supporting medical imaging and laboratory testing. It can be difficult to confirm, especially early on, since the signs and symptoms may be similar to those of other medical problems. The McDonald criteria, which focus on clinical, laboratory, and radiologic evidence of lesions at different times and in different areas, is the most commonly used method of diagnosis with the Schumacher and Poser criteria being of mostly historical significance. While the above criteria allow for a non-invasive diagnosis, some state that the only definitive proof is an autopsy or biopsy where lesions typical of MS are detected.

Clinical data alone may be sufficient for a diagnosis of MS if an individual has had separate episodes of neurologic symptoms characteristic of the disease. In those who seek medical attention after only one attack, other testing is needed for the diagnosis. The most commonly used diagnostic tools are neuroimaging, analysis of cerebrospinal fluid and evoked potentials. Magnetic resonance imaging of the brain and spine may show areas of demyelination (lesions or plaques). Gadolinium can be administered intravenously as a contrast agent to highlight active plaques and, by elimination, demonstrate the existence of historical lesions not associated with symptoms at the moment of the evaluation. Testing of cerebrospinal fluid obtained from a lumbar puncture can provide evidence of chronic inflammation in the central nervous system. The cerebrospinal fluid is tested for oligoclonal bands of IgG on electrophoresis, which are inflammation markers found in 75-85% of people with MS. The nervous system in MS may respond less actively to stimulation of the optic nerve and sensory nerves due to demyelination of such pathways. These brain responses can be examined using visual- and sensory-evoked potentials.

Secondary progressive MS occurs in around 65% of those with initial relapsing-remitting MS, who eventually have progressive neurologic decline between acute attacks without any definite periods of remission. Occasional relapses and minor remissions may appear. The most common length of time between disease onset and conversion from relapsing-remitting to secondary progressive MS is 19 years.

The primary progressive subtype occurs in approximately 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype. It is similar to the age that secondary progressive usually begins in relapsing-remitting MS, around 40 years of age. Progressive relapsing MS describes those individuals who, from onset, have a steady neurologic decline but also have clear superimposed attacks. This is the least common of all subtypes.

Unusual types of MS have been described; these include Devic's disease, Balo concentric sclerosis, Schilder's diffuse sclerosis, and Marburg multiple sclerosis. There is debate on whether they are MS variants or different diseases. Multiple sclerosis behaves differently in children, taking more time to reach the progressive stage. Nevertheless, they still reach it at a lower average age than adults usually do.

Although there is no known cure for multiple sclerosis, several therapies have proven helpful. The primary aims of therapy are returning function after an attack, preventing new attacks, and preventing disability. As with any medical treatment, medications used in the management of MS have several adverse effects. Alternative treatments are pursued by some people, despite the shortage of supporting evidence.

During symptomatic attacks, administration of high doses of intravenous corticosteroids, such as methylprednisolone, is the usual therapy, with oral corticosteroids seeming to have a similar efficacy and safety profile. Although, in general, effective in the short term for relieving symptoms, corticosteroid treatments do not appear to have a significant impact on long-term recovery. The consequences of severe attacks that do not respond to corticosteroids might be treatable by plasmapheresis.

As of 2014, nine disease-modifying treatments have been approved by regulatory agencies for relapsing-remitting multiple sclerosis (RRMS) including: interferon β-1a, interferon β-1b, glatiramer acetate, mitoxantrone, natalizumab, fingolimod, teriflunomide, dimethyl fumarate and alemtuzumab. Their cost effectiveness as of 2012 is unclear.

In RRMS they are modestly effective at decreasing the number of attacks. The interferons and glatiramer acetate are first-line treatments and are roughly equivalent, reducing relapses by approximately 30%. Early-initiated long-term therapy is safe and improves outcomes. Natalizumab reduces the relapse rate more than first-line agents; however, due to issues of adverse effects is a second-line agent reserved for those who do not respond to other treatments or with severe disease. Mitoxantrone, whose use is limited by severe adverse effects, is a third-line option for those who do not respond to other medications. Treatment of clinically isolated syndrome (CIS) with interferons decreases the chance of progressing to clinical MS. Efficacy of interferons and glatiramer acetate in children has been estimated to be roughly equivalent to that of adults. The role of some of the newer agents such as fingolimod, teriflunomide, and dimethyl fumarate, as of 2011, is not yet entirely clear.

No treatment has been shown to change the course of primary progressive MS and as of 2011 only one medication, mitoxantrone, has been approved for secondary progressive MS. In this population tentative evidence supports mitoxantrone moderately slowing the progression of the disease and decreasing rates of relapses over two years.

D. Treatments Involving Agonism

In another embodiment, the disclosure contemplates enhancing the engagement of VLA-4 and VEGFR2 with syndecan-1 or active fragments thereof. Peptides having this activity would need, at a minimum, to contain the binding site for both of these molecules, which are found between residues 210 and 236 of syndecan-1. Any shorter molecules, such as 210-233 (SEQ ID NO: 4) or 214-236 (SEQ ID NO: 7), would be incapable of agonism. In particular, this agonism would be applied to endothelial cells that express both VLA-4 and VEGFR2.

Wound healing, or wound repair, is an intricate process in which the skin (or another organ-tissue) repairs itself after injury. In normal skin, the epidermis (outermost layer) and dermis (inner or deeper layer) exists in a steady-state equilibrium, forming a protective barrier against the external environment. Once the protective barrier is broken, the normal (physiologic) process of wound healing is immediately set in motion. The classic model of wound healing is divided into three or four sequential yet overlapping phases: (1) hemostasis, (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis).

In the inflammatory phase, bacteria and debris are phagocytosed and removed, and factors are released that cause the migration and division of cells involved in the proliferative phase.

The proliferative phase is characterized by angiogenesis, collagen deposition, granulation tissue formation, epithelialization, and wound contraction. In angiogenesis, new blood vessels are formed by vascular endothelial cells. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

In the maturation and remodeling phase, collagen is remodeled and realigned along tension lines and cells that are no longer needed are removed by apoptosis. However, this process is not only complex but fragile, and susceptible to interruption or failure leading to the formation of chronic non-healing wounds. Factors which may contribute to this include diabetes, venous or arterial disease, old age, and infection. The phases of wound healing normally progress in a predictable, timely manner; if they do not, healing may progress inappropriately to either a chronic wound such as a venous ulcer or pathological scarring such as a keloid scar.

Treatment of wounds depends on how severe the wound is, its location, and whether other areas are affected. If another condition is causing problems with wound healing, it is important to treat or control this problem. A caregiver may prescribe antibiotics to fight infection, either orally, i.v., or applied directly on the wound area. Palliative care such as for pain, swelling and fever are often prescribed. Wound care is essential as well and includes cleansing, debridement and wound dressing. Dressings are particularly important to protect the wound from further injury and infection. These may also help give pressure to decrease swelling. Dressings may be in the form of bandages, films, or foams. They may contain certain substances that may help promote faster healing. Sometimes, skin taken from another part of the body may be used to close a large wound. The skin may also be man-made, which contains special cells needed to repair damaged tissues. Additional treatments include hyperbaric oxygen therapy (HBO), negative pressure therapy (also called vacuum-assisted closure or "VAC"), or creams, ointments, or medicines with special solutions which help in wound healing may be applied to the wound.

V. COMBINATION THERAPIES

A. Cancer

Tumor cell resistance to DNA damaging agents represents a major problem in clinical oncology. One goal of current cancer research is to find ways to improve the efficacy of chemo- and radiotherapy. One way is by combining such traditional therapies with gene therapy. In the context of the present disclosure, it is contemplated that syndecan peptide therapy could be used similarly in conjunction with chemotherapeutic, radiotherapeutic, or immunotherapeutic intervention.

To kill cells, inhibit cell growth, inhibit metastasis, inhibit angiogenesis or otherwise reverse or reduce the malignant phenotype of tumor cells, using the methods and compositions of the present disclosure, one would generally contact a target cell with a syndecan peptide and at least one other therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both agents, or by contacting the cell with two distinct compositions or formulations, at the same time, wherein one composition includes the syndecan peptide and the other includes the agent.

Alternatively, the syndecan treatment may precede or follow the other treatment by intervals ranging from minutes to weeks. In embodiments where the other treatment and the syndecan peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) pass between the respective administrations.

It also is conceivable that more than one administration of either the syndecan peptide or the other therapy will be desired. Various combinations may be employed, where the syndecan peptide is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both therapies are delivered to a cell in a combined amount effective to kill the cell.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the disclosure, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use with in combination with peptides of the present disclosure. For example, selective estrogen receptor antagonists ("SERMs") include Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with peptides, as described above.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present disclosure.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors affect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the local or regional delivery of syndecan peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining syndecan therapies with chemo- and radiotherapies, combinations with immunotherapy, hormone therapy, toxin therapy and surgery are also contemplated. In particular, one may employ targeted therapies such as Avastin, Erbitux, Gleevec, Herceptin and Rituxan.

It also should be pointed out that any of the foregoing therapies may prove useful by themselves in treating cancer.

B. Prevention of Scarring/Abberrant Wound Healing

In other embodiments, one may use peptides of the present disclosure in combination with other therapies to prevent scarring. These include corticosteroids, laser therapy, cryosurgery and interferon ca.

C. Inflammatory and Autoimmune Diseases

Inflammatory and autoimmune diseases may be treated in combinations including peptides of the present disclosure and other agents, such as steroids, NSAIDs, anti-inflammatory cytokines, or any other agents mentioned as first line therapies for these conditions.

D. Promoting of Wound Healing

In the context of the present disclosure, it is contemplated that syndecan-1 or a fragment retaining the ability to facilitate VLA-4 interaction with VEGFR2 may be used in combination with a second therapeutic agent to more effectively treat wounds. Additional therapeutic agents contemplated for use in combination with syndecan-1 or active fragments thereof include, but are not limited to other wound healing agents, protective agents, and scar reducing agents and the like. Specific examples include corticosteroids, cytotoxic drugs, antibiotics, antiseptics, nicotine, anti-platelet drugs, NSAIDS, colchicines, anti-coagulants, vasoconstricting drugs and immunosuppressives, as well as HBO and VAC methods, discussed above.

To aid in the wound healing process, using the methods and compositions of the present disclosure, one would generally contact a cell with syndecan-1 or an active fragment thereof in combination with a second agent. These compositions would be provided in a combined amount effective to exert a combined effect on the damaged tissue. This process may involve contacting the cells with syndecan-1 or active fragment, in combination with a second therapeutic agent or factor(s) at the same time. This may be achieved by contacting the cell with a single composition or pharmacological formulation that includes both agents, or by contacting the cell with two distinct compositions or formulations, at the same time, wherein one composition includes the syndencan-1 or active fragment and the other includes the second agent.

Alternatively, treatment with syndecan-1 or active fragments, or salts or analogs thereof, may precede or follow the additional agent treatment by intervals ranging from minutes to weeks. In embodiments where the second agent is applied separately to the target, one would generally ensure that a significant period of time did not expire between the time of each delivery, such that the agent would still be able to exert an advantageously combined effect on the target. In such instances, it is contemplated that one would contact the target with both modalities within about 12-24 hr of each other and, more preferably, within about 6-12 hr of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of the peptides described herein in combination with a second therapeutic agent will be desired. Various combinations may be employed, where the syndencan-1 or fragment is "A" and the second therapeutic agent is "B", as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated.

In the present disclosure, a number of drugs or agents may prove particularly useful when combined with syndencan-1. Such agents/drugs include corticosteroids, NSAIDs or any other anti-inflammatory, a cytotoxic drug, an antibiotic, antimicrobial, antifungal or antiseptic, nicotine, an anti-platelet drug, colchicine, anti-coagulants, vasoconstricting drugs or immunosuppressives.

VI. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Reagents.

SST0001, an N-acetylated glycol split heparin is a potent inhibitor of HPSE and was kindly provided by Sigma-tau Industrie Farmaceutiche Riunite S.p.A. (Pomezia, Italy). S1ED$^{210-240}$ peptide from GeneScript Corporation (location) was reconstituted in DME medium (Invitrogen) 200 mM HEPES (pH7.4) (Sigma). VEGFR2 inhibitor Vandetanib (ZD6474) was obtained from LC Laboratorues (Woburn, Mass., USA). VEGF165 was obtained from PeproTech (Rocky Hill, N.J., USA). Recombinant GST and GST-mouse-S1ED proteins were prepared as previously described (Beauvais et al., 2004a; 2004b). Rabbit anti-pY$^{1175}$ VEGFR2 serum (mAb 19A10) and rabbit anti-VEGFR2 (mAb 55B11) were obtained from Cell Signaling Technology (Danvers, Mass., USA). Mouse anti-human VEGFR2 serum (CH-11) and mouse anti-α4-integrin (P1H4) were obtained from Millipore. Polyclonal antibodies against human Sdc1 were affinity-purified as previously described (Beauvais et al., 2004a). All secondary antibodies were purchased from Jackson ImmunoResearch (West Grove, Pa., USA). Mouse anti-human MMP-9 (clone 6-6B) antibody was from Calbiochem.

Cell Culture.

All cell lines were cultured at 37° C. with 7.5% $CO_2$, 92.5% air and 85% humidity. CAG myeloma cells, established at the Myeloma Institute for Research and Therapy (Little Rock, Ark., USA), were transfected with empty vector (HPSE$^{low}$ cells) or vector containing the cDNA for human HPSE (HPSE$^{high}$ cells) as described. P3×63Ag8 mouse myeloma cells were from the ATCC. Cells were grown in RPMI1640 (Invitrogen) with 10% fetal bovine serum (Atlanta Biologicals, Lawrenceville, Ga., USA), 4 mM L-glutamine (Fisher Scientific), and 0.05 mM β-mercaptoethanol (Sigma). HMEC-1 were kindly provided by Drs. E. W. Ades and F. J. Candal (Center for Disease Control, Atlanta, Ga., USA) and Dr. T. J. Lawley (Emory University, Atlanta, Ga., USA. HMEC-1 cells were grown in MCDB131 medium (Mediatech, Manassas, Va., USA) supplemented with 5 mM L-glutamine, 20 mM $NaHCO_3$, 10 ng/ml epidermal growth factor, 1 pg mL hydrocortisone, bovine brain extract with heparin and antibiotics (Single-Quot kit; Lonza, Walkersville, Md., USA) and 15% fetal bovine serum (Atlanta Biologicals, Lawrenceville, Ga., USA).

Cell Spreading Assay.

Nitrocellulose-coated slides were coated for 2 hr at 37° C. with 40 μg/ml FN (kindly provided by Dr. Donna Peters, University of Wisconsin-Madison) or 5 μg/ml recombinant VCAM-1/Fc chimera (R&D Systems) in calcium and magnesium-free PBS (CMF-PBS; 135 mM NaCl, 2.7 mM KCl, 10.2 mM $Na_2HPO_4$-$7H_2O$ and 1.75 mM $KH_2PO_4$, pH7.4). Slides were blocked for 1 hr at 37° C. with RPMI 1640 containing 1% heat-denatured BSA (plating medium). Cells in plating medium were allowed to attach and spread for 2.5 hr at 37° C. Slides were fixed in 4% EM grade paraformaldehyde (Electron Microscopy Sciences) in CMF-PBS and labeled for 30 min in 0.13 μM rhodamine phalloidin (Invitrogen) in CMF-PBS. Coverslips were mounted in non-fluorescing mounting medium (Immumount; Thermo Shandon) and allowed to dry. All images were acquired with a Nikon Microphot FX microscope using a 20× objective (Nikon; Ex 541-551, DM 580, Barrier 590), Photometric CoolSnap ES camera, and version 7.7.3.0 Metamorph© Imaging software (Molecular Devices). All images represent results from triplicate wells and at least three independent experiments.

Immunostaining.

Fixed cells on FN-coated slides were quenched with 0.1 M glycine, permeabilized with CMF-PBS containing 0.1% Triton X-100 for 3 min at room temperature (RT) and blocked with 5% BSA in CMF-PBS. Cells were stained with primary antibodies to α4-integrin (P1H4), VEGFR2 (mAb 55B11), VEGFR2 (CH-11) or GST for 2 hr at RT, rinsed in CMF-PBS, incubated for 1 hr with secondary antibodies (Alexa-488-conjugated goat anti-mouse IgG (H+L) F(ab')$_2$ and Alexa-546-conjugated goat anti-rabbit IgG (H+L) F(ab')$_2$ secondary antibody (Molecular Probes) (1:100 dilution) in blocking buffer, followed by washing in CMF-PBS and double-distilled $H_2O$ before mounting in Immumount. All images represent results from triplicate wells and at least three independent experiments. Images were processed and colorized using Adobe Photoshop (Adobe Systems).

Migration Assay.

The bottom chambers of Transwell filter chambers (8 μm pores; Corning) were coated with 40 μg/ml of FN. Cells (5×10$^5$ in 0.2 ml plating medium) were placed in the upper chamber and incubated for 16 hr at 37° C. in the $CO_2$ incubator. After incubation, cells in the upper chamber were removed and cells on the bottom side of the filter were fixed in 4% paraformaldehyde (PFA) and stained with 0.1% Crystal Violet before imaging. Cells from at least five random fields were counted.

Time-Lapse Live Cell Imaging.

HPSE$^{low}$ cells or HPSE$^{high}$ cells were plated in FN-coated 48-well plates in plating medium and allowed to attach and spread for 2.5 hr. After washing, attached cells were observed at 37° C. on a Nikon Eclipse TE2000U microscopy system equipped with environment chamber using a PlanApo 20× objective (0.75 numerical aperture) and a Photometrics CoolSnap ES camera. Cells were tracked with Metamorph and Images were collected at 10 min intervals over 4 hr.

Immunoprecipitation.

HPSE$^{low}$ cells were plated on FN in the presence of 4 µg/ml GST or GST-S1ED for 2.5 hr. The cells were washed with CMF-PBS, then lysed for 20 min on ice in lysis buffer (0.5% Triton X-100 in 50 mM Hepes, 50 mM NaCl and 10 mM EDTA (pH 7.4) containing a 1:1000 dilution of protease inhibitor mixture set III (Calbiochem). Cell lysates were precleared at 13000 rpm for 20 min at 4° C. using 50 µg/ml isotype-matched nonspecific IgG and 30 µl of protein G agarose (GE Healthcare), then incubated at 4° C. overnight with either 10 µg/ml anti-α4-integrin (P1H4) or VEGFR2 (mAb 55B11) or nonspecific mouse IgG. Immunoprecipitated α4-integrin or VEGFR2 were dissolved in SDS sample buffer), electrophoresed and analyzed on western blots as described previously. Visualization of immunoreactive bands was performed using ECF reagent (Amersham Pharmacia) to detect alkaline-phosphatae-conjugated probing antibody and scanned on a Typhoon Trio Variable Mode Imager (GE Healthcare).

GST Pull Down Assay.

CAG cells were washed with CMF-PBS and then lysed for 20 min on ice in lysis buffer. Cell debris was removed by centrifugation at 13000 rpm for 20 min at 4° C. Whole cell lysates were then incubated at 4° C. overnight with either 3 µM GST or 3 µM GST-S1ED in the absence or presence of 1 µM, 3 µM, and 10 µM S1ED$^{210-240}$ peptide. GST or GST-S1ED was captured by addition of glutathione Sepharose and the beads were washed with ice-cold lysis buffer and CMF-PBS, prior to addition of SDS-PAGE sample buffer and analyzed by electrophoresis and western blotting as described previously.

Example 2—Results

Adhesion and Spreading of CAG Cells on FN or VCAM-1 is Enhanced by HPSE.

Myeloma cells expressing high levels of HPSE are more invasive than cells expressing low levels of the enzyme (Yang et al., 2002; Mahtouk et al., 2007 and Yang et al., 2005). To test whether such cells also display increased adhesion to FN and VCAM-1, cell adhesion ligands expressed in the myeloma tumor niche, CAG myeloma cells transfected with the cDNA for HPSE and expressing high levels of the enzyme (HPSE$^{high}$) were compared to cells transfected with empty vector alone that express low endogenous levels (HPSE$^{low}$). When plated onto FN or VCAM-1, both cell types were observed to attach equally (FIGS. 1A-B). However, HPSE$^{high}$ cells spread rapidly and form a polarized morphology, whereas the majority of the HPSE$^{low}$ cells do not (FIGS. 1A-B). To confirm that the spreading of HPSE$^{high}$ cells is attributed to HPSE expression, HPSE was inhibited by pre-treatment with the HPSE inhibitor SST0001 (Ritchie et al., 2011). This treatment blocked HPSE$^{high}$ cell spreading on FN and VCAM-1, but had no effect on attachment of either cell type (FIGS. 1A-B).

FN and VCAM-1 are ligands for the α4-integrin (VLA-4), which is expressed on myeloma cells (Sanz-Rodriguez et al., 1999). Thus, the inventors questioned whether VLA-4 mediates the adhesion and spreading that they observe. Blocking of VLA-4 with a function-blocking antibody, clone P1H4, resulted in complete inhibition of cell attachment of both HPSE$^{high}$ and HPSE$^{low}$ cells (FIG. 1B).

Many cell types, including myeloma cells, that constitutively express high levels of HPSE respond over time with altered gene expression, due both to enzymatic and nonenzymatic activities of HPSE (Zetser et al., 2003; Levy-Adam et al., 2008; Goldshmidt et al., 2003 and Sotnikov et al., 2004). To test whether the polarized phenotype of the HPSE$^{high}$ cells was due to altered gene expression in response to long-term constitutive expression of this enzyme, or was a more immediate response to trimming of heparan sulfate (HS) chains during the adhesion and spreading event, HPSE$^{low}$ and HPSE$^{high}$ cells were treated for 2 hr with heparinase III (HPIII), a bacterial enzyme that completely degrades the HS (Desai et al., 1993), before plating on FN and VCAM-1. Destruction of the HS by HPIII induces spreading of HPSE$^{low}$ cells comparable to that observed for HPSE$^{high}$ cells (FIG. 1C). In sum, these data suggest that trimming of HS chains during VLA-4-mediated adhesion to FN and VCAM-1 activates a cell polarization response in the CAG cells. The bipolar morphology displayed by the HPSE$^{high}$ cells is typical of motile cells (Ridley, 2011; Ridley et al., 2003). To test this, the inventors examined cell migration towards FN in serum-free medium using a Transwell migration assay (Keely, 2001). HPSE$^{high}$ cells efficiently migrated toward FN, whereas HPSE$^{low}$ cells failed to do so (FIG. 1D).

Shed Sdc1 Mediates the HPSE-Enhanced Effect in CAG Cells.

Trimming of the HS chains on Sdc1 by HPSE induces MMP9-mediated shedding (Yang et al., 2007 and Ramani et al., 2012). To test whether Sdc1 shedding might have a role in the HPSE-induced motility of the CAG cells, HPSE$^{low}$ and HPSE$^{high}$ cells were plated on VCAM-1 in the absence or presence of an MMP9 blocking antibody. The blocking antibody effectively blocks the polarized spreading of HPSE$^{high}$ cells on VCAM-1 without disrupting adhesion (FIG. 2A). To confirm that Sdc1 is shed in response to MMP9 cleavage, HPSE$^{low}$ and HPSE$^{high}$ cells were grown in suspension at equal densities with or without 10 µg/ml MMP9 blocking antibody (clone 6-6B). After 48 hr, the conditioned media were harvested and shed Sdc1 was visualized on a western blot (FIG. 2B). Higher amounts of Sdc1 were detected in the conditioned medium of HPSE$^{high}$ cells compared to HPSE$^{low}$ cells, but is reduced to control levels by MMP9 blocking antibody (FIG. 2B).

To test whether the shed Sdc1 protein or HS chains are responsible for the altered phenotype of the HPSE$^{high}$ CAG cells, the inventors questioned whether recombinant GST-tagged Sdc1 ectodomain (GST-S1ED) expressed in bacteria and devoid of HS could mimic the effect of MMP9 cleavage. GST-S1ED was added to HPSE$^{high}$ cells in the presence or absence of MMP9 blocking antibody. As expected, the spreading of the HPSE$^{high}$ cells is blocked in the presence of MMP9 blocking antibody. However, the polarized phenotype is rescued by GST-S1ED addition (FIG. 2C), even in the presence of the MMP9 inhibitor.

These findings suggest that the Sdc1 ectodomain contains an active site that promotes the invasive phenotype. To identify this putative site, deletions and truncations were introduced into the GST-S1ED construct and the mutant proteins were tested in the spreading assay using HPSE$^{low}$ cells plated on VCAM-1 (FIG. 3A). Full length GST-SLED, GST-S1ED$^{175-249}$, GST-S1ED$^{175-240}$, GST-S1ED$^{210-249}$ and GST-S1ED$^{200\text{-}240}$ induced cell spreading. However, GST-S1ED$^{17\text{-}195}$, GST-S1ED$^{175\text{-}194}$ and GST-S1ED$^{175\text{-}212}$ did not, implicating a putative active site spanning amino acids 210-240 (FIGS. 3A-B). Testing this prediction by deletion of amino acids 210-240 (GST-S1ED$^{\Delta 210\text{-}240}$) also abolishes the ability of GST-S1ED to induce cell spreading, confirming this as the active region (FIG. 3B). To test if this region is not only necessary, but also sufficient to induce the invasive phenotype, HPSE$^{low}$ cells were treated with a peptide corresponding to amino acids 210-240, S1ED$^{210\text{-}240}$. As shown in FIG. 3C, the S1ED$^{210\text{-}240}$ peptide is sufficient to induce HPSE$^{low}$ cell spreading on VCAM-1. Further truncation of this peptide demonstrates that S1ED$^{210\text{-}236}$ retains full activity, whereas S1ED$^{210\text{-}233}$ or S1ED$^{214\text{-}240}$ do not (FIG. 3C). Thus, the amino acids 210-213 and 234-236 are critical for the invasive phenotype (highlighted in red in FIG. 3B).

HPSE Expression Leads to Activation of VEGFR2 when VLA-4 Engages Ligand.

Next, the inventors questioned how the shed Sdc1 promotes the myeloma cell invasive phenotype. They have shown previously that Sdc1 acts as an organizer for other cell surface receptors, including receptor tyrosine kinases (RTKs) (Rapraeger et al., 2013; Wang et al. 2010; Beauvais and Rapraeger, 2010). The inventors hypothesized that amino acids 210-236 in the ectodomain of Sdc1 may be a site that organizes and activates RTKs. To test this hypothesis, they treated HPSE$^{high}$ cells with various RTK inhibitors to identify an RTK responsible for this phenotype. They found that blockade of vascular endothelial growth factor receptor-2 (VEGFR2) kinase activity with Vandetanib completely inhibits HPSE$^{high}$ cell spreading on FN (FIG. 4A). This treatment did not affect the adhesion of either the HPSE$^{low}$ or HPSE$^{high}$ cells (FIG. 4A). CAG cells are known to produce VEGF as an autocrine growth factor and it has been shown to promote the disease (Kumar et al., 2003; Giatromanolaki et al., 2010; Purushothaman et al., 2010). To test whether activation of VEGFR2 by exogenous VEGF also promotes polarized spreading of the cells, VEGF was added to HPSE$^{low}$ cells plated on FN. Surprisingly, addition of VEGF failed to induce spreading of the cells. Likewise, blocking VEGF binding to VEGFR2 with a blocking antibody failed to block the invasive phenotype observed in the HPSE$^{high}$ cells (FIG. 4A). In sum, VEGFR2 activation appears to be critical for the altered phenotype but VEGFR2 activation is independent of VEGF, suggesting a novel Sdc1-dependent mechanism for activation of VEGFR2 in the myeloma cells.

The inventors next questioned whether VEGFR2 is upstream (e.g., responsible for shedding) or downstream (e.g., a target of the shed Sdc1) of Sdc1 shedding by testing whether or not Sdc1 mimetic peptide could rescue Vandetinib-blocked spreading. HPSE$^{high}$ cell spreading on FN was inhibited using either anti-MMP9 blocking antibody or Vandetanib in the presence or absence of S1ED$^{210\text{-}236}$. As observed earlier (cf. FIGS. 3A-C), S1ED$^{210\text{-}236}$ rescued spreading in the presence of MMP9 inhibitor (FIG. 4B). However, it fails to rescue spreading blocked by Vandetanib (FIG. 4B), suggesting that VEGFR2 activity is required for a step downstream of MMP9-induced Sdc1 shedding. To directly test whether or not VEGFR2 is a target that is activated by Sdc1, HPSE$^{low}$ cells were suspended or plated on FN in the presence or absence of S1ED$^{210\text{-}236}$. VEGFR2 activation was assessed by measuring autophosphorylation at Tyr1054/1059 in its kinase domain (Lamalice et al., 2007). When HPSE$^{low}$ cells are treated with the peptide while in suspension, there is no alteration of VEGFR2 phosphorylation (FIG. 4C, left). However, S1ED$^{210\text{-}236}$ peptide causes VEGFR2 phosphorylation in HPSE$^{low}$ cells plated on FN (FIG. 4C, left), to which they adhere via VLA-4 (cf, FIG. 1B).)

S1ED 210-236 Causes Capture of VEGFR2 by VLA-4.

Having established that S1ED$^{210\text{-}236}$ induces VEGFR2 activation in an adhesion-dependent manner, the question remains why VEGFR2 activation depends on shed Sdc1 and VLA-4-mediated adhesion. One possibility is that shed Sdc1 couples VEGFR2 to VLA-4 that is clustered to sites of FN or VCAM-1 engagement, thereby clustering and activating VEGFR2 by transphosphorylation. To test this, HPSE$^{high}$ cells were plated on FN, then immunostained for VLA-4 and VEGFR2. The inventors found that the integrin and VEGFR2 co-localize on the protrusive lamellipodium (FIG. 5A). Next, they tested whether this co-localization would be induced by Sdc1 extracellular domain. For this, HPSE$^{low}$ cells were plated on FN in the presence of GST-S1ED to induced polarized spreading, then were immunostained for VLA-4, VEGFR2 and the GST tag on S1ED to see where the S1ED was localized. As shown in FIG. 5B, GST-S1ED co-localized with VEGFR2 or VLA-4 at the protrusive lamellipodium. The Sdc1-mediated association of VEGFR2 with VLA-4 was further confirmed by immunoprecipitation (FIG. 5C). VEGFR2 immunoprecipitated from HPSE$^{low}$ cells plated on FN failed to precipitate VLA-4. However, VLA-4 is co-immunoprecipitated with VEGFR2 from HPSE$^{low}$ cells plated on FN in the presence of GST-S1ED.

The Inhibitory Peptides Block the HPSE-Induced Invasive Phenotype.

As a final confirmation of the role of Sdc1 in the HPSE-induced invasive phenotype, the inventors tested whether or not high concentrations of the S1ED$^{210\text{-}240}$ peptide would block the HPSE-induced invasive phenotype of HPSE$^{high}$ cells. As proof of principle, the effect of S1ED$^{210\text{-}240}$ peptide was further tested on cell migration through a Transwell filter coated with FN. FN-induced migration in HPSE$^{high}$ cells was decreased by treatment with 30 µM S1ED$^{210\text{-}240}$. Although the peptide induced migration of HPSE$^{low}$ cells at low concentrations (e.g., 0.3-3 µM), it failed to induce at 30 µM, suggesting that it inactivates rather than activates the mechanism at this concentration. To define which amino acids within this peptide are necessary to activate and inhibit the HPSE induced invasive phenotype, three peptides containing truncations from the N- or C-terminus were tested, e.g., S1ED$^{210\text{-}236}$, S1ED$^{210\text{-}233}$, S1ED$^{214\text{-}240}$ (shown in FIG. 6B). Only S1ED$^{210\text{-}236}$ induces HPSE$^{low}$ cell spreading equal to that observed with S1ED$^{210\text{-}240}$, suggesting that it retains the minimal sequence for this activity (FIG. 6D) and confirming the results shown in FIG. 3C These data suggest that amino acids 234-236 (PVD) and 210-213 (DFTF) (shown in red in FIG. 6B) are necessary to activate the mechanism. Interestingly, S1ED$^{210\text{-}236}$ and S1ED$^{210\text{-}233}$ block cell adhesion at high concentrations (30 µM), suggesting that they disrupt VLA-4 affinity or avidity. This inhibition is independent of VEGFR2 and does not depend on Sdc1 shedding, since the Sdc1 is not shed in the absence of HPSE expression, nor is VEGFR2 active on these cells. This suggests that these peptides potentially block VLA-4 activity even on cells that are not being induced to invade by HPSE. S1ED$^{214\text{-}240}$, which lacks the N-terminal DFTF sequence, does not cause cell spreading or block adhesion, suggesting that the DFTF sequence that it lacks may be specific for binding VLA-4.

Turning to the HPSE$^{high}$ cells, which are already induced to spread by shed Sdc1, the inventors found that S1ED$^{210\text{-}236}$ and S1ED$^{210\text{-}233}$ block cell spreading when added at increasing concentrations, but these concentrations also induce cell detachment, suggesting that they affect VLA-4-mediated adhesion and making it difficult to assess whether they specifically disrupt the spreading mechanism (FIG. 6E). However, it is readily observed that S1ED$^{214-240}$ blocks the spreading of HPSE$^{high}$ cells because it has no effect on cell adhesion (FIG. 6E). Regardless of mechanism, these three peptides disrupt the adhesion and/or invasive phenotype of the HPSE$^{high}$ cells. This is confirmed by testing invasion directly on FN-coated transwell filters (FIG. 6F). Whereas HPSE$^{high}$ cells are observed to migrate through the filter, S1ED$^{210-236}$, S1ED$^{210-233}$ and S1ED$^{214-240}$ all reduce migration by 60-80%, similar to inhibition of VEGFR2 signaling using vandetanib (FIG. 6F).

To test whether the different abilities of the peptides to inhibit adhesion and/or spreading reflected their abilities to interact with VLA-4 or VEGFR2, they were used as competitors during capture of VEGFR2 or VLA-4 by GST-S1ED (FIG. 6G). GST-S1ED captures both VLA-4 and VEGFR2 when incubated with CAG myeloma cell lysates. S1ED$^{210-236}$ effectively blocks capture of both receptors when used at 30 µM. In contrast, S1ED$^{214-240}$ only competes for capture of VEGFR2, confirming that the N-terminal DFTF sequence is necessary for binding VLA-4 and competing with its capture by SLED. Conversely, S1ED$^{210-233}$ competes for capture of VEGFR2, identifying the C-terminal PVD motif as the VEGFR2 capture site.

Similar studies were conducted with P3×63Ag8 mouse myeloma cells (P3× cells) in order to further test the inhibitory properties of S1ED$^{210-233}$ (SEQ ID No: 4) and S1ED$^{214-236}$ (SEQ ID No: 7), peptides that lack either the VLA-4 or VEGFR2 binding sites, respectively. As expected, S1ED$^{210-233}$ blocks the adhesion of the myeloma cells to FN, whereas S1ED$^{214-236}$ is without effect (FIG. 7A). However, the invasion of the P3X cells through filters coated with FN is blocked by either peptide (FIG. 7B), confirming the requirement for both VLA-4 activation and VEGFR2-coupling to active VLA4 by Sdc1 to acquire the invasive phenotype. Treatment with inhibitors confirms that this invasion depends on HPSE, VLA-4 and VEGFR2 activation (FIG. 7B).

VLA-4 and VEGFR2 are normally expressed on vascular endothelial and lymphatic cells, suggesting that the mechanism observed in myeloma is part of a normal mechanism in the vasculature. Using immortal HMEC-1 vascular endothelial cells as a model system, the inventors found that these cells express levels of HPSE equivalent to the HPSE$^{high}$ myeloma cells (FIG. 8A). Conditioned medium from the HMEC-1 cells contains shed Sdc1 and this shedding is prevented by the HPSE inhibitor SST0001 (FIG. 8B). Furthermore, recombinant GST-S1ED captures VLA-4 and VEGFR2 from HMEC-1 cells lysates (FIG. 8C), similar to capture observed in myeloma cells. HMEC-1 cells plated on the IIICs fragment of FN, a specific VLA-4 ligand, spread rapidly during a 2 hr spreading assay (FIG. 8D). VLA-4 and Sdc1 co-localize to sites in the spreading margins of the cells, as do Sdc1 and VEGFR2, or VLA-4 and VEGFR2, indicating that these three receptors form a ternary complex at these sites. Binding and spreading is completely dependent on VLA-4, as inhibition of this integrin with VLA-4 or β1-integrin specific antibodies prevents adhesion (FIG. 8E). Furthermore, the VLA-4 dependent spreading is dependent on the HPSE-induced shedding of Sdc1 and activation of VEGFR2, as it is prevented by HPSE inhibitor, MMP-9 blocking antibody, and vandetanib, as well as by S1ED$^{210-233}$ and S1ED$^{214-240}$ (FIG. 8E). As with the myeloma cells, blocking of VEGF binding to VEGFR2 has no effect. HMEC-1 cells plated on IIICS activate VEGFR2, as observed by monitoring pY1175 on western blots, and this activation is disrupted by 10 M S1ED peptides expected to block the invasive phenotype. This is confirmed by transwell invasion assays on Fn coated filters, in which blockade of VLA-4 (P1H4 antibody), inhibition of HPSE (SST0001), blockade of Sdc1 shedding (anti-MMP9), blockade of VEGFR2 activation (vandetanib) or S1ED$^{210-233}$, S1ED$^{214-240}$ or S1ED$^{210-236}$ all block invasion (FIG. 8G). Last, the inventors tested the ability of the peptides to block angiogenesis using the in vitro tube formation assay (FIG. 8H). HMEC-1 cells plated on matrigel containing 100 µg/ml FN overnight form the typical honeycomb network of endothelial tubules. Tube formation on this matrix is not enhanced by VEGF. Inhibition of HPSE, or addition of S1ED$^{210-236}$, S1ED$^{210-233}$, or S1ED$^{214-240}$, blocks tube formation, demonstrating a role of the Sdc1-coupled VEGFR2 mechanism in angiogenesis.

As a final test of peptide stability and efficacy in vivo, the S1ED$^{210-240}$ peptide (called SSTN$_{210-240}$ because it is being used as an inhibitor), which inhibits the mechanism at 30 µM concentrations, was delivered systemically to mice bearing human breast cancer (SKBr3) xenografts at a concentration estimated to reach 30 µM in the blood. The peptide effectively reduced the size of the tumors (FIG. 9), potentially by blocking the VLA-4/VEGFR2 mechanism necessary for tumor-induced angiogenesis upon which these tumor rely.

Example 3—Discussion

Multiple myeloma is an incurable cancer in which high expression of shed Sdc1 is linked to poor outcome. Expression of HPSE, which trims the HS chains on Sdc1 leading to increasing expression of shed Sdc1 leads to aggressive disease and poor outcome. However, the molecular mechanisms underlying the bioactivity of shed Sdc1 remain largely unknown. In the present study, the inventors reveal that shed Sdc1 activates VEGFR2 to promote an invasive phenotype. Mechanistically, the native, membrane anchored Sdc1 engages VLA-4 and is required for it to form high affinity adhesions with its ligands, the matrix ligand FN or stromal cell/endothelial cell receptor VCAM-1. When Sdc1 is shed, it acquires the additional ability to mediate VEGFR2 interaction with VLA-4 clustered to these adhesion sites, leading to VEGFR2 activation. This requires VLA-4 clustering to these adhesion sites. This traces to an active site, aa210-236, in the Sdc1 ectodomain that can be mimicked by a short peptide encompassing this sequence, or can be inhibited for shorter peptides comprising parts of this sequence that either interact with VLA-4 alone and block adhesion, or interact with VEGFR2 alone and block its activation.

HPSE acts as a tumor promoter via enzymatic as well as non-enzymatic means. However, its enzymatic activity is required for the invasive phenotype described here. Accumulating evidence suggests that such trimming may de-protect Sdc1 for recognition by other proteins (Ramani et al., 2012). In the current example, the trimming appears to expose Sdc1 to MMP9, shown previously to cause shedding of the proteoglycan from the surface of HPSE-expressing myeloma cells when its HS chains are trimmed (Purushothaman et al., 2008; Ramani et al., 2012). This HPSE-stimulated release of bioactive Sdc1 has been shown to promote tumor growth and metastasis in vivo (Yang et al., 2002 and Yang et al., 2007). In the mechanism defined here, the inventors find that the shed Sdc1 activates VEGFR2 in a ligand-independent manner; although VEGFR2 is typically expressed on endothelial cells, its expression is aberrantly upregulated in a number of tumor types, including myeloma (Kumar et al., 2003).

Another key feature of this mechanism is VLA-4. VLA-4 participates in myeloma cell adhesion to ILDV (Ile-leu-Asp-Val) and QIDS (Gln-Ile-Asp-Ser) motifs in FN and VCAM-1, respectively (Noborio-Hatano et al., 2009; Sanz-Rodriguez et al., 1999; Michigami et al., 2000; Imai et al., 2010; Vacca et al., 1995). Multiple myeloma is characterized by the formation of multiple lytic lesions throughout the skeleton, suggesting dissemination of myeloma cells via continuous entry into and extravasation from the microvasculature. Myeloma cells encounter VCAM-1 on endothelial cells within the microvasculature during their dissemination, and VCAM-1 and FN are found on stromal cells and in the matrix, respectively, within the bone marrow (Sanz-Rodriguez et al., 1999; Vande Broek et al., 2008). VLA-4 engagement has multiple roles in advancement of MM, as it promotes bone resorption by osteoclasts by up-regulating the release of the osteoclast-activating cytokines macrophage inflammatory protein (MIP)-1α and MIP-1β (Abe et al., 2009; Michigami et al., 2000), promotes cell adhesion-mediated drug resistance (CAM-DR), which can be overcome in part by Bortezomib-induced downregulation of integrin expression (Nororio-Hatano et al., 2009).

The findings here suggest that shed Sdc1 promotes the engagement of VEGFR2 with matrix-bound VLA-4, leading to VEGFR2 activation. The means by which VEGFR2 is activated may trace to integrin clustering. The affinity of integrins for their ligands is mediated partly by their activation, driven by inside-out signaling, and partly by avidity, a consequence of active integrin clustering via interactions within their transmembrane domains. The inventors' finding that VEGFR2 is activated by Sdc1 only on adherent cells, and not on cells in suspension, suggests that clustering of the integrin serves to cluster and activate VEGFR2 as well. Indeed, activation of VEGFR2 by VEGF in the absence of shed Sdc1 fails to cause the invasive phenotype, ostensibly because VEGFR2 is not associated with the integrin. This suggests that the integrin, VEGFR2 and the syndecan must physically be associated for activation to occur. In this regard, the activation mechanism is similar to another receptor complex organized by Sdc1, namely, the Sdc1-IGF-1R-αvβ3 or αvβ5 integrin complex (Beauvais et al., 2009; Beauvais et al., 2010). IGF-1R is activated by clustering of the complex via Sd1 to sites of matrix adhesion, leading to an IGF-1R-generated inside-out signal that activates the integrin. This activation does not require IGF1, although IGF1 can enhance the signal. However, displacement of IGF-1R from the ternary receptor complex blocks its ability to activate the integrin, even if IGF-1R itself is activated by IGF1. In the current example involving VEGFR2, it appears that VLA-4 is already active due to its engagement with Sdc1, but its coupling to VEGFR2 when Sdc1 is shed leads to VEGFR2 activation and altered downstream signaling from the VLA-4/VEGFR2 complex that causes the highly invasive phenotype. Active integrin appears localized to the leading edge of a protrusive lamellipodium that characterizes these invasive cells. VEGFR2 is likely to co-localize with the integrin at these sites when the two receptors are coupled by shed Sdc1, a mechanism that can be recapitulated by adding exogenous recombinant GST-S1ED to HPSE$^{low}$ myeloma cells.

Interestingly, the VEGFR2 is not activated by native, membrane-anchored Sdc1. This also sets this mechanism apart from Sdc1-coupled IGF-1R, which requires the Sdc1 to be membrane bound. Although the reason for this is not known, the inventors speculate that release of the Sdc1 from its membrane anchorage may be necessary for the protein to re-orient such that is can retain its interaction with the integrin, but simultaneously fit a binding pocket on VEGFR2. IGF-1R coupling to human syndecans requires a.a. 93-120 (92-119 in mouse), which is distal to the membrane proximal a.a. 210-236 site necessary for VEGFR2 activation. It is interesting to note that bioactive juxtamembrane sites exist in other syndecans as well. A site in Sda4 (87-131) originally described by McFall and Rapraeger has been shown to have several highly conserved amino acids that mediate b1-integrin-dependent attachment of fibroblasts (Whiteford et al., 2008). Whiteford has also described a site in Sdc2 that appears responsible for PTP activity. Whether more than one site exists in these other syndecans, making them multifunctional organizers of receptor signaling as the inventors now describe in Sdc1, remains to be seen.

The fact that shed Sdc1 permeates the tumor microenvironment in myeloma suggests that it may have a role in VEGFR2 activation on other cell types. These findings suggest that it plays a prominent role during angiogenesis mediated by vascular endothelial cells, which also express VLA-4 integrin along with VEGFR2. Note that HPSE expression has also been documented in activated endothelial cells, suggesting a potential role for Sdc1 shedding in VLA-4 and VEGFR2 signaling even in the absence of tumor cells. The inventors' prior work has demonstrated a role for shed Sdc1 derived from the conditioned medium of HPSE$^{high}$ myeloma cells in the induction of angiogenesis, both in an aortic ring outgrowth assay and in HUVEC sprouting to form microvessels in matrigel. This activity was dependent on VEGF, the HS on the Sdc1, and the Sdc1 core protein itself. At least part of the bioactivity of the core protein appeared to trace to its role in activating IGF-1R, which is necessary for VEGF-stimulated VEGFR2 activity and is blocked by SSTN$_{92-119}$. The current findings suggest that the 210-236 site identified here also has a role.

In summary, the inventors have identified a mechanism by which HPSE expression in myeloma cells leads to activation of VEGFR2 and an invasive phenotype. The phenotype depends on coupling VEGFR2 to VLA-4 via an active site (residues 210-236) in shed Sdc1. Peptides containing this sequence, or containing a partial sequence capable of engaging VLA-4 or VEGFR2 alone, act as potent inhibitors of this mechanism. They can inhibit by preventing the association of VEGFR2 with VLA-4, or, as shown for S1ED$^{210-233}$ and S1ED$^{210-236}$, can prevent VLA-4 from functioning by preventing its engagement with Sdc1, regardless of whether the syndecan is shed or not. This mechanism in which VEGFR2 is coupled to VLA-4 by Sdc1 is likely to have a role in the invasion of myeloma cells during intravasion and extravasation in which the cells encounter FN in the bone marrow microenvironment, and VCAM-1 on the surface of endothelial cells lining the vasculature or on stromal cells with the marrow. Although described on myeloma cells, the mechanism may also be operative on other cancers where HPSE is known to act as a tumor promoter, and during angiogenesis. The peptides that block the mechanism have significant potential as therapeutics to target cancer and other diseases that depends on this mechanism. Furthermore, the peptides that target VLA-4 alone and disrupt its adhesion ability may target yet other immune, vascular or cancer cells where VLA-4 functions independently of VEGFR2 and/or Sdc1.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent they provide exemplary procedural or details supplementary to those set forth herein, are incorporated herein by reference:

Abe et al., *J Bone Miner Metab* 27: 16-23, 2009.
Alexander et al., *Nat. Genet.*, 25:329-332, 2000.
Alon and Feigelson, *Semin. Immunol.* 14:93-104, 2002.
Alon et al., *J. Cell. Biol.* 128:1243-53, 1995.
Anttonen et al., *Br. J. Cancer,* 79:558-564, 1999.
Baciu and Goetinck, *Mol. Biol. Cell,* 6:1503-1513, 1995.
Barash et al., *FEBS J,* 277(19): p. 3890-903, 2010.
Barbareschi et al., *Cancer,* 98:474-483, 2003.
Bayer-Garner et al., *J. Cutan. Pathol.*, 28:135-139, 2001.
Beauvais and Rapraeger, *J. Cell Sci.*, 123(Pt 21): 3796-807 (2010).
Beauvais and Rapraeger, *Reprod Biol Endocrinol,* 2: p. 3, 2004.
Beauvais et al., *J Cell Biol,* 167(1): p. 171-81, 2004a.
Beauvais et al., *J Exp Med,* 206(3): p. 691-705, 2009.
Beauvais et al., *J. Cell Biol., Reprod. Biol. Endocrinol,* 2:3, 2004b.
Bernfield et al., *Annu. Rev. Biochem.*, 68:729-777, 1999.
Bernfield et al., *Annu. Rev. Cell Biol.*, 8:365-393, 1992.
Bodanszky et al., *J. Antibiot.,* 29(5):549-53, 1976.
Burbach et al., *Matrix Biol.,* 22:163-177, 2003.
Carey et al., *Exp. Cell Res.,* 214:12-21, 1994a.
Carey et al., *J. Cell Biol.,* 124:161-170, 1994b.
Cohen et al., *J. Med. Chem.,* 33:883-894, 1990.
Conejo et al., *Int. J. Cancer,* 88:12-20, 2000.
Couchman et al., *Int. Rev. Cytol.,* 207:113-150, 2001.
Crescimanno et al., *J. Pathol.,* 189:600-608, 1999.
Damiano and Dalton, *Leuk Lymphoma* 38: 71-81, 2000.
Damiano et al., *Blood* 93: 1658-1667, 1999.
David et al., *J. Cell Biol.,* 118(4):961-969, 1992.
Desai et al., *Biochemistry,* 32(32): p. 8140-5, 1993.
Fujiya et al., *Jpn. J. Cancer Res.,* 92:1074-1081, 2001.
Garmy-Susini et al., *Proc. Nat'l Acad. Sci. USA* 110:9042-9047, 2013.
Garmy-Susini et al., *Cancer Res.* 70:3042-51, 2010.
Garmy-Susini et al., *J. Clin Invest.* 115:1542-51, 2005.
Giatromanolaki et al., *Anticancer Res,* 30(7): p. 2831-6, 2010.
Goldshmidt et al., *FASEB J,* 17(9): p. 1015-25, 2003.
Granes et al., *Exp. Cell Res.,* 248:439-456, 1999.
Gronenborn et al., *Anal. Chem.,* 62(1):2-15, 1990.
Hansen et al., *J. Cell Biol.,* 126:811-819, 1994.
Hirabayashi et al., *Tumour Biol.,* 19:454-463, 1998.
Iba et al., *J. Cell Biol.,* 149:1143-1156, 2000.
Imai et al., *Int J Hematol* 91: 569-575, 2010.
Inki and Jalkanen, *Ann. Med.*, 28:63-67, 1996.
Izzard et al., *Exp. Cell Res.,* 165:320-336, 1986.
Jackson, *Seminars in Oncology,* 24:L164-172, 1997.

Johnson et al., *In: Biotechnology And Pharmacy,* Pezzuto et al. (Eds.), Chapman and Hall, NY, 1993.
Jones et al., *J. Med. Chem.,* 39:904-917, 1996.
Kato et al., *Mol. Biol. Cell,* 6:559-576, 1995.
Keely, *Methods Enzymol,* 333: p. 256-66, 2001.
Kelly et al., *Cancer Res,* 63(24): p. 8749-56, 2003.
Khan et al., *J. Biol. Chem.,* 263:11314-113148, 1988.
Khotskaya et al., *J Biol Chem,* 284(38): p. 26085-95, 2009.
Kim et al., *Mol. Biol. Cell,* 5:797-805, 1994.
Klass et al., *J. Cell Sci.,* 113:493-506, 2000.
Klatka, *Eur. Arch. Otorhinolaryngol.,* 259:115-118, 2002.
Kumar et al., *Leukemia,* 17(10): p. 2025-31, 2003.
Kumar-Singh et al., *J. Pathol.,* 186:300-305, 1998.
Lamalice et al., *Circ Res,* 100(6): p. 782-94, 2007.
Laubach et al., *Med Oncol,* 27 Suppl 1: p. S1-6, 2010.
Lebakken and Rapraeger, *J. Cell Biol.,* 132:1209-1221, 1996.
Leppa et al. *Cell Regul.,* 2:1-11, 1991.
Leppa et al., *J. Cell Sci.,* 109:1393-1403, 1996.
Leppa et al., *Proc. Natl. Acad. Sci. USA,* 89:932-936, 1992.
Levy et al., *Br. J. Cancer,* 74:423-431, 1996.
Levy et al., *Bull. Cancer,* 84:235-237, 1997.
Levy-Adam et al., *PLoS One,* 3(6): p. e2319, 2008.
Levy-Adam et al., *Semin Cancer Biol,* 20(3): p. 153-60, 2010.
Liu et al., *J. Biol. Chem.,* 273:22825-22832, 1998.
Mahtouk et al., *Blood,* 109(11): p. 4914-23, 2007.
Martinelli et al., *Haematologica,* 86(9): p. 908-17, 2001.
Matsumoto et al., *Int. J. Cancer,* 74:482-491, 1997.
McFall and Rapraeger, *J. Biol. Chem.,* 272:12901-12904, 1997.
McFall and Rapraeger, *J. Biol. Chem.,* 273:28270-28276, 1998.
McPherson, *J. Biol. Chem.,* 251:6300-6306, 1976.
McQuade et al., *J Cell Sci,* 119(Pt 12): p. 2445-56, 2006.
Meads et al., *Clin Cancer Res,* 14(9): p. 2519-26, 2008.
Merrifield, *J. Am. Chem. Soc.,* 85:2149-2154, 1963.
Michigami et al., *Blood* 96: 1953-1960, 2000.
Miranti and Brugge, *Nat. Cell Biol.,* 4:E83-90, 2002.
Mundhenke et al., *Am. J. Pathol.,* 160:185-194, 2002.
Nakaerts et al., *Int. J Cancer,* 74:335-345, 1997.
Nakanishi et al., *Intl. J. Cancer,* 80:527-532, 1999.
Navia et al., *Curr. Opin. Struct. Biol.,* 2:202-210, 1992.
Noborio-Hatano et al., *Oncogene* 28: 231-242, 2009.
Numa et al., *Int. J. Oncol.,* 20:39-43, 2002.
O'Connell et al., *Am J Clin Pathol,* 121(2): p. 254-63, 2004.
Ohtake et al., *Br. J. Cancer,* 81:393-403, 1999.
Orpana and Salven, *Lymphoma* 43:219-224, 2002.
Park et al., *J. Biol. Chem.,* 277:29730-29736, 2002.
PCT Appln. PCT/US00/03745
PCT Appln. PCT/US00/14667
PCT Appln. PCT/US99/11913
PCT Appln. PCT/US99/18441
Peptide Synthesis, 1985
Protective Groups in Organic Chemistry, 1973
Protein NMR Spectroscopy, Principles and Practice, J. Cavanagh et al., Academic Press, San Diego, 1996.
Pulkkinen et al., *Acta Otolaryngol.,* 117:312-315, 1997.
Purushothaman et al., *Blood,* 115(12): p. 2449-57, 2010.
Purushothaman et al., *J Biol Chem,* 283(47): p. 32628-36, 2008.
Rajkumar et al., *Clin Cancer Res,* 6(8): p. 3111-6, 2000.
Rajkumar et al., *Clin Cancer Res,* 8(7): p. 2210-6, 2002.
Ramani et al., *J Biol Chem,* 287(13): p. 9952-61, 2012.
Rapraeger and Ott, *Curr. Opin. Cell Biol.,* 10(5):620-628, 1998.
Rapraeger et al., *FEBS J,* 280(10): p. 2194-206, 2013.

Rapraeger et al., *J. Cell Biol.*, 103:2683-2696, 1986.
Remington's Pharmaceutical Sciences, 15th Ed., 1035-1038 and 1570-1580, 1990.
Remington's Pharmaceutical Sciences, 15th Ed., 3:624-652, 1990.
Ria et al., *Leukemia*, 17(10): p. 1961-6, 2003.
Ridley et al., *Science*, 302(5651): p. 1704-9, 2003.
Ridley, *Cell*, 145(7): p. 1012-22, 2011.
Ritchie et al., *Clin Cancer Res*, 17(6): p. 1382-93, 2011.
Roskelley et al., *Curr. Opin. Cell Biol.*, 7:736-747, 1995.
Sanderson and Bernfield, *Proc. Natl. Acad. Sci. USA*, 85:9562-9566, 1988.
Sanderson and Borset, *Ann. Hematol.*, 81:125-135, 2002.
Sanderson and Yang, *Clin Exp Metastasis*, 25(2): p. 149-59, 2008.
Sanderson, *Semin. Cell Dev. Biol.*, 12:89-98, 2001.
Sanz-Rodriguez et al., *Br J Haematol*, 107(4): p. 825-34, 1999.
Schafmeister et al., *J. Amer. Chem. Soc.*, 122(24): 5891-5892, 2000.
Schnidrnaier et al., *Int J Biol Markers* 21: 218-222, 2006.
Scudla et al., *Neoplasma*, 57(2): p. 102-10, 2010.
Seidel et al., *Blood*, 95(2): p. 388-92, 2000.
Singer et al., *J. Cell Biol.*, 104:573-584, 1987.
Solid Phase Peptide Synthelia, 1984
Sotnikov et al., *J Immunol*, 172(9): p. 5185-93, 2004.
Stanley et al., *Am. J. Clin. Pathol.*, 112:377-383, 1999.
Streeter and Rees, *J. Cell Biol.*, 105:507-515, 1987.
Sun et al., *Int. J. Dev. Biol.*, 42:733-736, 1998.
U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Pat. No. 7,183,059
U.S. Pat. No. 7,192,713
U.S. Patent Publication 2005/0015232
Vacca et al., *Am J Hematol* 50: 9-14, 1995.
Vacca et al., *Br J Haematol*, 87(3): p. 503-8, 1994.
Vande Broek et al., *Clin Exp Metastasis*, 25(4): p. 325-34, 2008.
Vlodavsky et al., *Semin Cancer Biol*, 12(2): p. 121-9, 2002.
Wang et al., *J Biol Chem* 289: 30318-30332, 2014.
Wang et al., *J. Biol. Chem.*, 285:13569-13579, 2010.
Weber, *Advances Protein Chem.*, 41:1-36, 1991.
Whiteford et al., *J. Biol. Chem.* 283: 29322-29330, 2008.
Wider, *BioTechniques*, 29:1278-1294, 2000.
Wiksten et al., *Int. J. Cancer*, 95:1-6, 2001.
Woods and Couchman, *Curr. Opin. Cell Biol.*, 13:578-583, 2001.
Woods et al., *Embo J.*, 5:665-670, 1986.
Wu et al., *J Immunol*, 188(6): p. 2914-21, 2012.
Yamashita et al., *J. Immunol.*, 162:5940-5948, 1999.
Yang et al., *Blood*, 100(2): p. 610-7, 2002.
Yang et al., *Blood*, 105(3): p. 1303-9, 2005.
Yang et al., *J Biol Chem*, 282(18): p. 13326-33, 2007.
Yang et al., *Mol. Cell Biol.*, 30(22):5306-5317, 2010.
Zetser et al., *Cancer Res*, 63(22): p. 7733-41, 2003.

The invention claimed is:

1. A method of treating an inflammatory or autoimmune disease in a subject by inhibiting very late antigen-4 (VLA-4) interaction with syndecan-1, comprising contacting VLA-4 and/or syndecan-1 on the surface a cell within the subject that is associated with the inflammatory or autoimmune disease with a peptide segment consisting of between 12 and 100 amino acid residues and comprising amino acid residues 210-221, 210-233, 210-236, or 210-240 of SEQ ID NO:1; whereby the inflammatory or autoimmune disease is treated.

2. The method of claim 1, wherein the peptide segment is 12, 13, 14, 15, 16, 16, 17, 18, 19, 20, 21, 22, 23, 24, 25, 26, 27, 28, 29, 30, 31, 32, 33, 34, 35, 40, 45, 49, 50, 55, 60, 65, 70, 75, 80, 85, 90, 95 or 100 amino acid residues in length.

3. The method of claim 1, wherein the peptide segment is between 12 and 50 amino acid residues in length.

4. The method of claim 1, wherein the peptide segment is between 16 and 30 amino acid residues in length.

5. The method of claim 1, wherein the peptide segment is between 23 and 27 amino acid residues in length.

6. The method of claim 1, wherein the peptide segment consists essentially of amino acid residues 210-221 (SEQ ID NO:8), 210-233 (SEQ ID NO:4), 210-236 (SEQ ID NO:2), or 210-240 (SEQ ID NO:3) of SEQ ID NO:1.

7. The method of claim 1, wherein the peptide segment comprises amino acid residues 210-221 (SEQ ID NO:8), 210-233 (SEQ ID NO:4), 210-236 (SEQ ID NO:2), or 210-240 (SEQ ID NO:3) of SEQ ID NO:1.

8. The method of claim 1, wherein the peptide segment consists of amino acid residues 210-221 (SEQ ID NO:8), 210-233 (SEQ ID NO:4), 210-236 (SEQ ID NO:2), or 210-240 (SEQ ID NO:3) of SEQ ID NO:1.

9. The method of claim 1, wherein the cell is an endothelial cell or a lymphoid cell.

10. The method of claim 1, wherein contacting comprises providing an expression construct comprising a nucleic acid encoding the peptide segment.

11. The method of claim 1, wherein the inflammatory or autoimmune disease that is treated is ulcerative colitis, Crohn's disease, rheumatoid arthritis, systemic lupus erythematosus (SLE), or multiple sclerosis (MS).

* * * * *